(12) United States Patent
Rade et al.

(10) Patent No.: US 7,282,488 B2
(45) Date of Patent: Oct. 16, 2007

(54) GENETIC ENGINEERING OF VASCULAR GRAFTS TO RESIST DISEASE

(75) Inventors: Jeffrey J. Rade, Baltimore, MD (US); Antony Y. Kim, Elliott City, MD (US); Richard H. Sohn, Laurel, MD (US)

(73) Assignee: The Johns Hopkins Univeristy, Baltimore, MD (US)

( * ) Notice: Subject to any disclaimer, the term of this patent is extended or adjusted under 35 U.S.C. 154(b) by 0 days.

(21) Appl. No.: 09/863,803

(22) Filed: May 22, 2001

(65) Prior Publication Data

US 2002/0068713 A1  Jun. 6, 2002

Related U.S. Application Data

(60) Provisional application No. 60/206,162, filed on May 22, 2000.

(51) Int. Cl.
*A61K 48/00* (2006.01)

(52) U.S. Cl. ............... 514/44; 435/320.1; 435/69.1; 435/455

(58) Field of Classification Search ............. 514/44; 424/93.21; 435/320.1
See application file for complete search history.

(56) References Cited

U.S. PATENT DOCUMENTS

| | | | |
|---|---|---|---|
| 5,571,786 A * | 11/1996 | Eibl et al. | |
| 5,804,392 A * | 9/1998 | Esmon et al. | 435/7.1 |
| 5,852,171 A * | 12/1998 | Fukudome et al. | 530/350 |
| 6,290,949 B1 * | 9/2001 | French et al. | |
| 6,309,380 B1 * | 10/2001 | Larson et al. | |
| 6,399,064 B1 * | 6/2002 | Fukudome et al. | |

FOREIGN PATENT DOCUMENTS

| | | |
|---|---|---|
| WO | WO 92/07573 | 5/1992 |
| WO | WO 93/13807 | 7/1993 |
| WO | WO 96/05303 | 2/1996 |
| WO | WO 96/06933 | 3/1996 |
| WO | WO 97/30083 | 8/1997 |

OTHER PUBLICATIONS

Kim et al. Early loss of thrombomodulin expression impairs vein graft thromboresistance implications for vein graft failure pp. 205-212 2002.*
Valley et al. Supplement II Circulation vol. 104, No. 17 2001.*
Miller et al. Targeted vectors for gene therapy pp. 190-199 vol. 9 1995.*
Deonarain Ligand-targeted receptor-mediated vectors for gene delivery pp. 53-69 1998.*
Newby et al. Targets for gene therapy of vein grafts pp. 489-494 1999.*
Bowie et al, Science Mar. 1990; 247:1306-10.*
Rudinger, Peptide Hormones 1976; Jun. pp. 1-7.*
Thomas et al, Transplant 1999;68:1660-73.*
Stephens et al, J Autoimmun 1997;10:293-8.*
Skolnick et al. TIBTECH Jan. 2000;18:34-9.*
Vassalli et al, Cardiovasc Res 1997,35:459-69.*
Game et al, Wien Klin Wochenschr 2001;113:823-38.*
Platt et al, Nat Biotech Mar. 2002;20(3)231-2.*
Hardy et al, J Virol 1997;71:1842-9.*
Qing et al, J Virol 1997;71:5663-7.*
Newby et al, Curr Opin Cardiol 1999;14:489-94.*
Soares et al, J Immunol 1998;161:4572-82.*
Kim et al, Circ Res 2002;90:205-12.*
Dittman, et al. 1990. "Structure and Function of Thrombomodulin" Blood 75, No. 2: pp. 329-336.
C. Esmon. 1989. "The Roles of Protein C and Thrombomodulin in the Regulation of Blood Coagulation" J. of Biol. Chem. vol. 264, No. 9: 4743-4746.
Lundell, et al. 1999. "Reduction in Vascular Lesion Formation by Hirudin Secreted From Retrovirus-Transduced Confluent Endothelial Cells on Vascular Grafts in Baboons" Circulation 100: 2018-2024.
Motwani, et al. 1998. "Aortocoronary Saphenous Vein Graft Disease" Circulation 97:916-931.
Rade, et al. 1996. "Local Adenoviral-Mediated Expression of Recombinant Hirudin Reduces Neointima Formation After Atreial Injury" Nature Medicine vol. 2, No. 3: 293-298.
Waugh, et al. 2000. "Thrombomodulin Overexpression to Limit Neointima Formation" Circulation 102: 332-337.
Waugh, et al. 1998. "Local Overexpression of Thrombomodulin for In Vivo Prevention of Arterial Thrombosis in a Rabbit Model" Circ Res 84: 84-92.
Rade, et al. 1998. "Retroviral Vector-Mediated Expression of Hirudin By Human Vascular Endothelial Cells: Implications for the Design of Retroviral Vectors Expressing Biologically Active Proteins" Gene Therapy 6: 385-392.
PCT International Search Report, 4 pages.
Lin, et al., "Modulation of Glycosaminoglycan Addition in Naturally Expressed and Recombinant Human Thrombomodulin"; The Journal of Biological Chemistry, vol. 269, No. 40, pp. 25021-25030, 1994.
Tsiang, et al., "Functional Domains of Membrane-bound Human Thrombomodulin"; The Journal of Biological Chemistry, vol. 267, No. 9, pp. 6164-6170, 1992.
Kurosawa, et al., "Proteolytic Formation and Properties of Functional Domains of Thrombomodulin"; The Journal of Biological Chemistry, vol. 262, No. 5, pp. 2206-2212, 1987.

(Continued)

Primary Examiner—Q. Janice Li
(74) Attorney, Agent, or Firm—Peter F. Corless; Jonathan M. Sparks; Edwards Angell Palmer & Dodge LLP

(57) ABSTRACT

Disclosed are methods for treating a vascular graft that include introducing an effective amount of at least one nucleic acid encoding at least one agent that increases activated protein C (APC), expressing the agent in the cells; and increasing the APC sufficient to treat the blood vessel. Also provided are vascular grafts engineered to resist early and/or late graft failure.

28 Claims, 12 Drawing Sheets

OTHER PUBLICATIONS

Ye, et al., "The Fifth and Sixth Growth Factor-like Domains of Thrombomodulin Bind to the Anion-binding Exosite of Thrombin and Alter Its Specificity"; The Journal of Biological Chemistry, vol. 267, No. 16, pp. 11023-11028, 1992.

Kurosawa, et al., "A 10-kDa Cyanogen Bromide Fragment from the Epidermal Growth Factor Homology Domain of Rabbit Thrombomodulin Contains the Primary Thrombin Binding Site"; The Journal of Biological Chemistry, vol. 263, No. 13, pp. 5993-5996, 1988.

Clarke, et al., "The Short Loop between Epidermal Growth Factor-like Domains 4 and 5 Is Critical for Human Thrombomodulin Function"; The Journal of Biological Chemistry, vol. 268, No. 9, pp. 6309-6315, 1993.

Stearns, et al., "Microthrombomodulin"; The Journal of Biological Chemistry, vol. 264, No. 6, pp. 3352-3356, 1989.

Parkinson, et al., "Stable Expression of a Secretable Deletion Mutant of Recombinant Human Thrombomodulin in Mammalian Cells"; The Journal of Biological Chemistry, vol. 265, No. 21, pp. 12602-12610, 1990.

Regan, et al., "The Interaction between the Endothelial Cell Protein C Receptor and Protein C Is Dictated by the γ-Carboxyglutamic Acid Domain of Protein C"; The Journal of Biological Chemistry, vol. 272, No. 42, pp. 26279-26284, 1997.

Xu, et al., "Metalloproteolytic Release of Endothelial Cell Protein C Receptor"; The Journal of Biological Chemistry, vol. 275, No. 8, pp. 6038-6044, 2000.

Fukudome, et al., "Molecular Cloning and Expression of Murine and Bovine Endothelial Cell Protein C/Activated Protein C Receptor (EPCR)"; The Journal of Biological Chemistry, vol. 270, No. 10, pp. 5571-5577, 1995.

Fukudome, et al., "The Endothelial Cell Protein C Receptor"; The Journal of Biological Chemistry, vol. 271, No. 29, pp. 17491-17498, 1996.

J. M. Breuss, et al., "Adenoviral Gene Transfer of IkappaB Into Ballooned Rabbit Iliac Arteries For Prevention of Neointima Formation", Abstract, FASEB Journal, vol. 13, No. 4, 1999, 1 page.

Dennis E. Hallahan, "Nuclear Factor kB Dominant Negative Genetic constructs Inhibit X-ray Induction of Cell Adhesion Molecules in the Vascular Endothelium", Cancer Research, vol. 58, No. 23, 1998, 5 pages.

J. A. Brockman, et al., "Coupling of a Signal Response Domain in I-kappa-B-alpha to Multiple Pathways for NF-kappa-B Activation", Abstract, Molecular and Cellular Biol., vol. 15, No. 5, 1995, 1 page.

Ingrid H. C. Vos, et al., "NFkB decoy oligodexynucleotides reduce monocyte infiltration in renal allografts", FASEB Journal, vol. 14, No. 5, 2000, pp. 814-822.

Tam T. T. Huynh, et al., "Control of Intimal Hyperplasia By Local Modulation of NF-kB Activity In Experimental Vein Grafts", Abstract, Surgical Forum, vol. 48, 1997, 4 pages.

Giuseppe Vassalli, et al., "Gene therapy for arterial thrombosis", Cardiovascular Research, vol. 35, No. 3, 1997, Abstract, 11 pages.

Johannes Breuss, et al., "Adenoviral gene transfer of I-kappa-B into ballooned rabbit iliac arteries for prevention of restenosis" Abstract, Vascular Biology, vol. 96, No. 11, 2000, 1 page.

PCT International Search Report, 4 pages, May 1, 2002.

\* cited by examiner

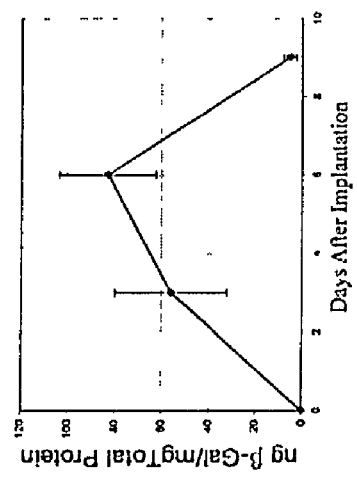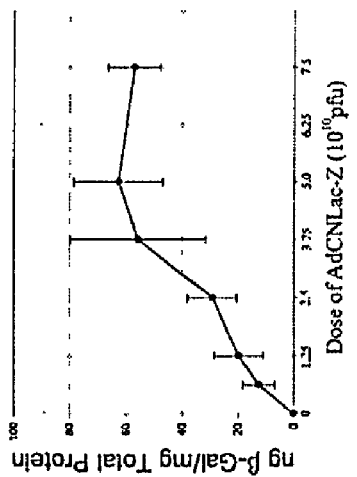
Fig. 6A
Fig. 6B
Fig. 6C

GENETIC ENGINEERING OF VASCULAR GRAFTS TO RESIST DISEASE

CROSS-REFERENCE TO RELATED APPLICATION

The present application claims the benefit of U.S. Provisional Application No. 60/206,162 filed on May 22, 2000, the disclosure of which is incorporated herein by reference.

FIELD OF THE INVENTION

The invention generally relates to genetic manipulation of blood vessels. More specifically, the invention provides methods for preventing or treating failure of vascular grafts in a host. Also provided are genetically engineered vascular grafts that resist such failure.

BACKGROUND

There is increasing recognition that failure of vascular grafts is a major medical problem. Particularly problematic have been saphenous vein grafts (SVG) used for coronary and peripheral arterial bypass surgeries. SVG feature obstructions related to thrombosis, neointimal hyperplasia and accelerated atherosclerosis that compromise graft patency. Patients receiving such grafts are at risk for profound medical problems including angina, myocardial infraction, the need for repeated percutaneous and surgical reveascularization procedures, and even death. See generally Motwani, J. G. and Topol, E. J. (1998) in *Cardiology* 97: 916; and Cameron, A. et al. (1996) in *N. Engl. J. Med.* 334: 216.

There is general recognition that failure of vascular grafts can be divided into two categories ie., early and late. Early graft failure (occurring within the first few months after implantation) is typically due to occlusive thrombosis. Late graft failure (occurring months to years after implantation) is due to neointimal hyperplasia and the development of accelerated atherosclerosis.

Thrombomodulin (TM) has been reported to be an important anticoagulant molecule expressed in abundance by the endothelial cell lining of all blood vessels. TM has been reported to reduce or block thrombosis due to its ability to mediate the activation of the circulating anticoagulant molecule, protein C. In a normal blood vessel, the small amount of thrombin that may be generated binds to TM expressed on endothelial cells. Binding of thrombin to TM converts thrombin's active site specificity such that it is no longer able to cleave fibrinogen to fibrin or activate cell-associated thrombin receptors. Thrombin bound to TM is, however, able to cleave protein C, thus generating activated protein C (APC). APC is a potent anticoagulant, which inhibits further thrombin generation by degrading several blood coagulation factors See eg., Jackman, R., et al., (1986) *Proc. Natl. Acad Sci. U.S.A.* 83:8834 and (1987) 84:6425.

There have been suggestions in the field that the level of TM expression and ability to activate protein C are important determinants of vascular thromboresistance. See eg., Mitchell C A et al (1986) *Thromb Haemost.* (1986) 56: 151; and Esmon, C T (1989) *J. Biol. Chem.* 264: 4743. Intravascular thrombosis occurs when the degree of local thrombin activation overwhelms the anticoagulant effects of the TM/APC pathway. Inherited or acquired defects in either TM or APC levels and/or function have been associated with pathologic thrombosis in humans. See Esmon C T (1989) *J. Biol. Chem.* 264: 4743 and references cited therein.

Denudation of the endothelial lining of arteries, as occurs during coronary or peripheral balloon angioplasty, is known to frequently result in occlusive thrombus formation as a result of enhanced local thrombin activation. Loss of TM activity and subsequent inability to generate APC consequent to endothelial cell denudation facilitates this local thrombin activation and contributes to vascular thrombus formation.

The endothelium of vein grafts implanted into the arterial circulation remains intact but appears to suffer a more subtle and chronic form of injury compared to that occurring during balloon injury of an artery. Although acute thrombosis occurs in up to 8 to 12% of SVG within the first month after implantation, little is known about the pathologic processes occurring to the endothelium that contribute to this. Specifically, little is known about changes in the expression or function of molecules that contribute to the thromboresistance of a normal blood vessel.

The neointima is understood to be a specific vessel layer that stereotypically develops after many forms of vascular injury. It is formed by proliferation and migration of smooth muscle cells out of the medial layer toward the vessel lumen. If unchecked, the neointima can encroach upon the lumen of the vessel resulting in the restriction of blood flow. In addition to causing vascular graft occlusion per se, the neointima is an avid substrate for the development of accelerated atherosclerosis.

Accelerated atherosclerosis is the major cause of late vein graft failure. Atherosclerotic plaques that develop in vascular grafts are prone to lumenal encroachment in identical fashion to plaques that develop in native arteries. Rupture of an atherosclerotic plaque in a coronary SVG can cause angina, myocardial infarction and death. Rupture of a plaque in a peripheral SVG can cause claudication and acute limb ischemia. In both cases, surgical or percutaneous procedures aimed at restoring graft patency often entails substantial risk to the patient and is frequently unsuccessful.

While the prevention of vascular graft failure is a worthwhile goal, few therapeutic options currently exist. (See Motwani J. and E. J. Topol (1998) *Circulation* 97: 916 and O. N. Nwasokwafor (1995) *Ann Intern Med* 123:528 for comprehensive reviews.) Given the prominent role of thrombosis, there have been some attempts to prevent vascular graft failure using systemic administration of antithrombotic or antiplatelet agents agents. Evidence suggests that use of such agents may marginally improve the survival of SVG, though they place the patient at risk for untoward bleeding risks. A more localized form of therapy that aggressively alters the prothrombotic phenotype of vascular grafts without concomitant adverse systemic effects is highly desirable.

Gene therapy methods, in particular, are increasingly recognized as a powerful tool for targeting the expression of pharmacologically active proteins to the vasculature. See eg., Schulick A H, et al. (1993) *Circ. Res.* 77: 475; Nabel E. G et al. (1990) *Science* 249: 1285; and Rafield, L. Et al. WO 92/07573.

See also Lim et al. (1991) *Circulation* 83: 2007; Flugelman et al., (1992) *Circulation* 85: 1110; Leclerc et al. (1992) *J. Clin. Invest.* 90: 936; Chapman et al. *Circ. Res.* 71: 27; Riessen et al. (1993) *Hum. Gene Ther.* 4: 749; Takeshita et al. *J. Clin. Invest.* (1994) 93: 652; Ohno T et al. (1994) *Science* 265: 781; von der Leyen, H. E. et al. *PNAS (USA)* (1995) 92: 1137.

Transfer of anti-sense nucleic acids that inhibit the expression of specific genes into arteries has also been reported. See Takeshita, S. et al. (1996) *Laboratory Invest.* 75: 487; and U.S. Pat. No. 5,652,225.

Viral mediated gene transfer is one preferred means of expressing anticoagulant molecules at the site of in vivo vascular injury. Results with first-generation replication defective adenovirus vectors have demonstrated that expression of the potent thrombin inhibitor, hirudin, can reduce thrombin-induced neointima formation following arterial injury without adverse systemic anticoagulant effects. See J. J. Rade et al. (1996) *Nature Medicine* 2: 293, for example.

In similar fashion, adenovirus-mediated gene transfer of TM to balloon injured arteries has been demonstrated to reduce both thrombus and neointima formation (J. M. Waugh et al. (1999) *Circ Res* 84:84 and (2000) *Circulation* 102:332). In this instance, balloon injury is expected to denude the arterial endothelium, the sole source of endogenous TM. It is not unexpected, therefore, that restoration of TM expression would decrease local thrombus formation and thrombin-induced neointima formation as was shown with adenovirus-mediated expression of hirudin (Rade, vida supra).

SUMMARY OF THE INVENTION

The invention generally relates to therapies for preventing or treating vascular graft failure. In one embodiment, the invention relates to therapeutic methods for addressing early graft failure by decreasing or eliminating local thrombin activation and subsequent occlusive thrombosis. In another embodiment, the invention provides therapies that reduce or eliminate the development of accelerated atherosclerosis, a predominant cause of late graft failure. The invention has a wide spectrum of useful applications including use in the prevention or treatment of saphenous vein graft (SVG) and synthetic graft failure in human patients.

The present invention is grounded in the discovery that restoring the capacity to generate activated protein C (APC) can improve graft patency by preventing local thrombin activation, inflammation and the development of accelerated atherosclerosis. More particularly, it has been found that increased APC generation can be accomplished directly, via viral-mediated transfer and expression of at least one agent for restoring or enhancing APC e.g, the thrombomodulin (TM) gene. Alternatively, increased APC generation can be achieved indirectly, via genetic manipulation of pathways that regulate TM expression. As discussed above, vascular graft failure can be divided temporally into early and late types. The increased APC generation provided by the invention addresses both types of failure. By preventing such failure, the invention substantially improves the morbidity and mortality associated with vascular graft failure.

Particular methods of the invention can be used to genetically engineer vascular grafts to restore or enhance APC generation. By restoring APC generation is meant establishing a level of APC that is at or near the level enzyme found in a corresponding (untreated) control graft. APC generation is enhanced when the level of APC exceeds that found in the control graft. Such engineered grafts are believed to provide better resistance to early and late graft failure. Examples are provided below of rabbit vein grafts genetically engineered with adenovirus vectors (Example-4), human saphenous vein grafts (SVG) genetically engineered with adeno-associated virus vectors (Example-7) and synthetic grafts seeded with genetically engineered endothelial cells (Example-14). Such grafts and their methods of manipulation can form the basis for novel treatments for patients suffering from a wide spectrum of graft disease, including failure of coronary or peripheral arterial bypass grafts.

Generally preferred invention practice involves increasing levels of APC in subject blood vessel grafts to improve patency and resist early and late type failure. That increase can be direct eg., by providing more APC enzyme to the graft either at one site or many sites within that graft. Alternatively, the increase can be indirect such as by manipulating cell or tissue pathways to produce more APC. In many embodiments, the invention involves increasing protein C (PC) activation to APC by contacting the grafts with at least one agent that facilitates such activation. Typically, but not exclusively, that activation of PC to APC will be local. That is, it will be substantially confined to the subject blood vessel graft. By providing for more PC activation in the grafts, more beneficial APC enzyme is made available. That enzyme, when made available to vascular grafts, is believed to help resist early and late types of graft failure.

Preferred invention methods generally restore graft APC generating activity to at least 50%, preferably to between 50% and 100% of that observed in normal arteries, or enhance graft APC generating activity by at least 120%, or more preferably by at least a about 200%, 300%, 500%, 1000%, 10,000% or more when compared to normal arteries as determined by what is referred to herein as a "standard activated protein C assay" or related phrase. Such assays are generally known in the field and are exemplified below.

The invention more particularly encompass methods that address early and/or late graft failure by administering to subject vascular grafts at least one agent for increasing APC therein, preferably less than ten of such agents, more preferably about two to five agents with about one or two agents being generally preferred. When more than one APC agent is desired, those agents can be administered to the grafts at the same time or different times as needed. Additionally preferred agents are derived from naturally-occurring constituents of blood vessel endothelium.

In one embodiment, the agent is thrombomodulin (TM), preferably mammalian TM, more preferably primate TM, and most preferably human TM; or a functional fragment thereof. For example, and without wishing to be bound to theory, it is believed that by providing more TM to the grafts, protein C is activated to APC (a potent anti-coagulant) thereby inhibiting local thrombin generation. Such local and especially robust inhibition of thrombin generation reduces or eliminates thrombus formation in subject vascular grafts. Preferred invention methods directly increase the TM activity by supplementing the grafts with more heterologous or homologous TM.

In invention embodiments in which at least one of the agents for increasing APC is TM (or a functional fragment thereof), that TM will be preferably restored to 50%, preferably to between 50% to 100% the levels found in normal arteries as determined by what is referred to herein as a "standard thrombomodulin detection" assay. Alternatively, the TM (or functional fragment) can increase the APC by at least about 25%, preferably between from about 50% to about 100%, more preferably at least about 150%, 200%, 300% or more when compared to normal arteries as determined by the standard thrombomodulin detection assay.

In another embodiment, the invention provides methods for addressing late graft failure that involve increasing APC in blood vessel grafts either directly (by providing more APC enzyme) or indirectly (by manipulating cell pathways to produce more APC). Such increased APC provided by the invention is believed to reduce or eliminate the development of accelerated atherosclerosis.

Such particular methods typically will provide a level of APC sufficient to provide at least about a 10% decrease in atherosclerosis compared to a non-treated (control) graft, preferably between from about 20% to about a 50% decrease, more preferably at least about an 85%, 90%, 95%, 99% or more decrease as determined by what is referred to herein as a "standard atherosclerotic rabbit vein graft model". See Example-13 (disclosing an example of the model in which foam cells can be counted by inspection).

Particular APC enhancing agents according to the invention include TM (as well as functional fragments thereof) as well as other agents that increase APC substantially independently of the TM ie., without significant involvement of thrombin binding. Examples of such agents are disclosed below and include identified endothelial cell protein C receptor (EPCR). Preferably, the receptor is mammalian EPCR, more preferably primate EPCR, and. Also included are specific transcription factors that are believed to reduce or eliminate undesired TM downregulation within subject vascular grafts.

More particular invention practice involves genetic modification of vein and arterial grafts to enhance APC enzyme directly or indirectly. For example, in one invention embodiment, the methods can be used to boost TM (or a functional fragment thereof) either alone or in combination with at least one other agent for increasing APC. Such methods are intended to help prevent, treat or reduce the severity of indications that are believed to endanger good vascular graft patency eg., thrombosis, neointimal hyperplasia and associated atherosclerosis.

Preferred for many invention applications are SVG grafts used for coronary and peripheral bypass surgeries and related procedures.

Accordingly, and in one aspect, the invention provides therapeutic methods for preventing or treating vascular graft failure by restoring or enhancing APC levels in the grafts when compared to a suitable (untreated) control vessel. More particular methods involve introducing into susceptible cells of the graft a therapeutically effective amount of at least one nucleic acid that encodes at least one agent for restoring or enhancing the APC. Such increased APC can be provided de novo in cases where subject grafts have little or no detectable APC or PC activation potential. However in most instances, the invention will augment endogenous APC or potential to activate PC by providing more APC to subject grafts. In one embodiment, the nucleic acid will encode human TM or a functional fragment thereof to restore or enhance APC enzyme in vascular grafts such as SVG.

Typically, the nucleic acid used in the method encodes at least one agent (usually an amino acid sequence) for restoring or enhancing APC. In some embodiments, the nucleic acid will encode distinct amino acid sequences eg., where a first sequence restores or enhances APC by one route and a second sequence restores or enhances that enzyme by a different route. As an illustration of this example of the invention, one of the agents can be human TM or functional fragment thereof while the other agent can be a mammalian PC receptor or functional fragment thereof. A preferred example is human EPCR. The nucleic acid is preferably introduced into susceptible cells of a blood vessel graft eg., endothelial cells, at a therapeutically effective level to enhance APC levels within the graft. Administration of any APC enhancing agent of the invention can be accomplished at the same or different times as needed to accomplish an intended graft result.

The present invention provides a variety of important advantages.

For example, preferred invention practice provides an especially potent anti-thrombin effect that significantly reduces or eliminates thrombus formation in vascular grafts. This feature is especially useful for reducing or eliminating early graft failure. Moreover, the enhanced APC levels provided by the invention positively impact risk from late graft failure due to the development of accelerated atherosclerosis.

In addition, the invention provides increased APC activity that is desirably robust and vessel-focused. Preferred practice involves genetic manipulation of subject vessels to increase APC locally, thereby avoiding side-effects that may arise from more global manipulation of that enzyme (eg., unwanted blood thinning).

As discussed, some invention embodiments employ multiple routes to enhance APC in the recipient blood vessel grafts. Particular invention methods boost TM levels and independently provide for more PC activation to make APC. In contrast, many prior methods have taken a more restricted (and less beneficial) approach by manipulating thrombomodulin expression, usually by only one route. Such limited approaches are believed to provide insufficient APC enzyme to subject vessels. In one embodiment, the invention addresses this shortcoming by enhancing APC by more than one route eg., by independently providing for enhanced levels of TM and APC in the blood vessel grafts. This and other invention strategies for increasing APC in the grafts has been found to provide an especially robust means of addressing early and late graft failure.

The invention provides other important advantages.

For example, the therapeutic methods of the invention are flexible and can be adapted readily to suit intended graft use. As an illustration, at least one step of the methods can be performed ex vivo. That is, one or more method steps can be conducted essentially outside of the mammal for which preserved graft patency is intended. Generally in this invention example, blood vessel grafts are removed from a donor or patient. Subsequently, such grafts are manipulated to introduce a therapeutically effective amount of at least one nucleic acid encoding at least one agent for increasing APC. Subsequently, the manipulated graft is implanted into the patient or another recipient in need of the blood vessel graft.

Preferably, at least the step of introducing or administering the nucleic acid to the recipient blood vessel graft is performed ex vivo although other steps may performed outside the mammal as needed. In this invention example, the method will often further include the step of transplanting the manipulated blood vessel graft into the mammalian host using one or a combination of conventional surgical techniques. The transplanting step can be performed as needed including, but not limited to, before introduction of the nucleic acid. In this example, the nucleic acid can be administered in vivo in accord with conventional genetic techniques. In other invention embodiments, some or all of the method steps are performed on the blood vessel in vivo.

Practice of the invention is compatible with a wide spectrum of agents that have or are suspected to enhance APC generation. Illustrative of agents include thrombomodulin (TM) as well as function fragments thereof. Additional agents, such as EPCR including functional fragments thereof, augment APC generation by "presenting" protein C to the TM-thrombin complex, thus making the activation process more efficient (Example-8). A combination of approaches is also contemplated (Example-9).

The invention also provides methods for engineering a vascular graft to resist graft failure in a mammal. The graft can be, but is not limited to, SVG. In one embodiment, the methods include at least one and preferably all of the following steps:

a) introducing into susceptible cells of the graft such as endothelial cells an effective amount of at least one nucleic acid encoding at least one agent that increases APC in cells of a blood vessel, b) expressing the agent in the cells; and c) increasing the APC in the graft to a level sufficient to resist graft failure.

Preferably, the level of APC in the engineered graft is sufficient to enhance blood vessel APC by at least about 20%, preferably between from about 50% to about 100%, more preferably at least about 200%, 300%, 500%, 1000%, 10,000% or more when compared to a non-treated (control) vessel as determined by the standard activated protein C assay.

Additionally preferred vascular grafts according to the invention exhibit a level of APC sufficient to provide at least about a 10% decrease the development of accelerated atherosclerosis compared to a non-treated (control) vessel, preferably between from about 20% to about a 50% decrease, more preferably at least about an 85%, 90%, 95%, 99% or more decrease as determined by what the standard atherosclerotic rabbit vein graft model. See the discussion below and Example-13.

In invention embodiments in which at least one of the agents for increasing APC in the engineered blood vessel is TM (or a functional fragment thereof), that TM will be preferably increased by at least about 25%, preferably between from about 50% to about 100%, more preferably at least about 150%, 200%, 300% or more when compared to a non-treated control vessel as determined by the "standard thrombomodulin detection" assay.

In another aspect, the present invention provides engineered vascular grafts suitable for use as grafts which vessels are made by one or a combination of methods described herein. Illustrative of such vessels is an autologous SVG or arterial vessel engineered to resist failure in a mammal and particularly a human patient.

The blood vessel grafts of the present invention provide important advantages.

For example, such grafts can be engineered to produce a pre-determined amount of APC. That is, the graft can be made to suit an intended graft use. Further, expression of the agent for enhancing APC can be constitutive or regulable as needed. The invention can thus provide mammals in need of graft treatment with an APC amount tailored to suit an existing or suspected medical condition impacting graft failure. Examples of such conditions include a family history of vessel occlusions, smoking, high cholesterol levels, as well as previous or ongoing exposure to anti-clotting drugs. In these instances, it may be desirable to make grafts having an especially robust anti-thrombin activity. In contrast, blood vessel grafts intended for patients without these conditions may require less APC. Accordingly, the invention is flexible and can be adapted to engineer blood vessel grafts that provide an appropriate level of APC activity.

Also provided by the invention are kits for performing the methods disclosed herein. Preferably, the kit includes at least one of the following components: a) at least one agent for increasing APC, preferably in which at least one of the agents is TM or a functional fragment thereof, and b) means for detecting at least one of: 1) expression of the agents in cells, and/or 2) increased APC enzyme in the blood vessel. More particular detection means include means for quantitation of protein C activity.

Other aspects of the invention are disclosed, infra.

BRIEF DESCRIPTION OF THE DRAWINGS

FIGS. 6A and 6B are graphs showing optimization of adenovirus-mediated gene transfer to rabbit vein grafts. The graphs show dose response (FIG. 6A) and duration of expression (FIG. 6B).

FIG. 6C is a photograph showing a macroscopic view of a lumenal surface of a rabbit vein graft transduced with a replication defective adenovirus expressing β-galactosidase.

DESCRIPTION OF PREFERRED EMBODIMENTS

Figure 1:
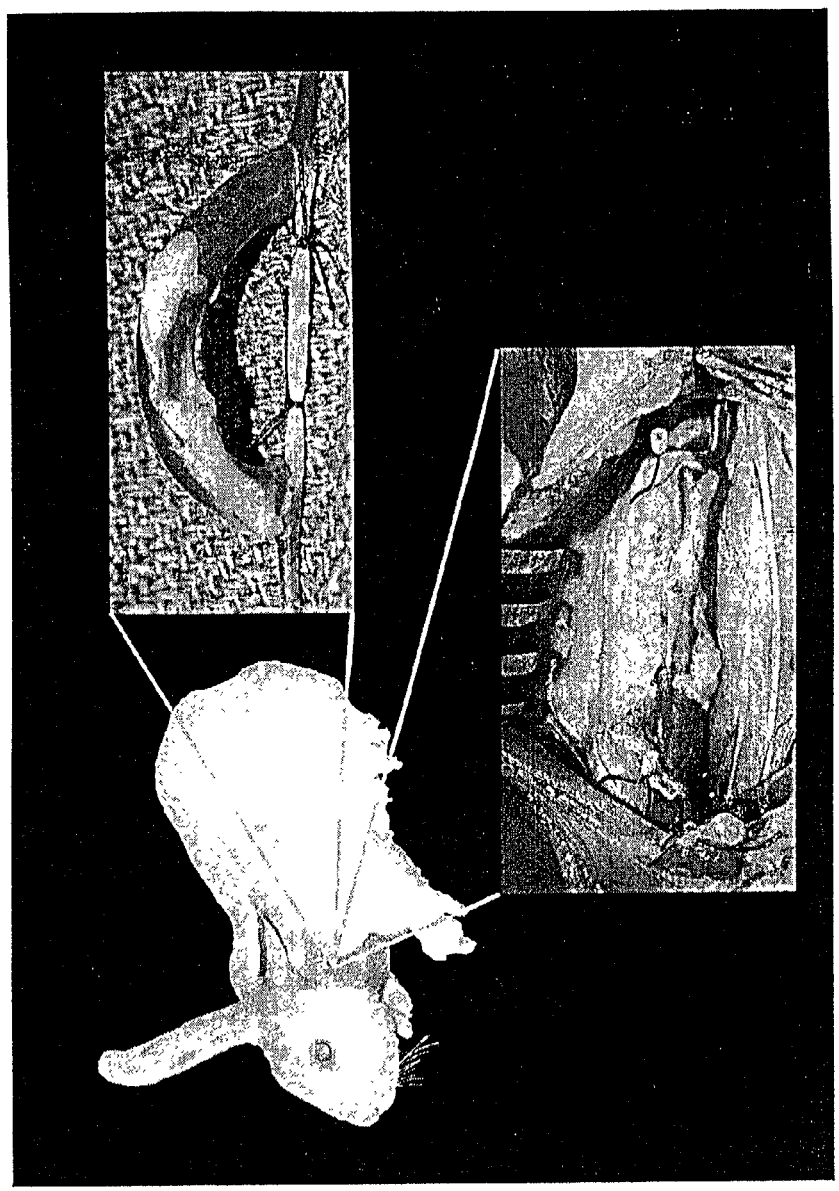
FIG. 1 is an illustration showing rabbit vein segments.

As discussed above, the invention relates to methods for preventing or treating vascular graft failure. Particular invention methods relate to therapies for reducing or eliminating early and/or late type failure. Methods of the invention generally provide at least one agent for enhancing activated protein C (APC) enzyme, thereby promoting preserved graft patency. The invention has a wide spectrum of useful applications including use in the prevention of saphenous vein graft (SVG) or synthetic graft failure in human patients.

By the phrase "vascular graft" is meant a vein or arterial graft. The word "graft", "implant" or "transplant" are used interchangeably to refer to biological vessel material derived from a donor for transplantation into a recipient. When used as a verb, the word "graft" is meant to refer to the act of placing such material into the recipient. The phrase "vascular graft" is also meant to embrace synthetic or semi-synthetic vascular material including artificial grafts seeded with naturally-occurring or recombinantly manipulated endothelial cells. Examples of such artificial grafts are provided in Example 14, below. A preferred vascular graft for many invention embodiments is a saphenous vein graft (SVG) manipulated in accord with this invention.

There is widespread recognition that atherosclerosis is a leading cause of death in many countries. Coronary and peripheral arterial bypass surgery is one treatment for atherosclerosis that usually cannot be treated with medicines or with balloon angioplasty. During the operation, saphenous veins removed from the leg are used as conduits to bypass the obstructed artery. In the U.S. alone, over 1 million saphenous vein grafts are implanted annually. Unfortunately, it has been reported that SVG fail at a significantly higher high rate than do native arterial grafts eg., internal mammary arteries (IMG). Failure is related to development of occlusive blood clots. Those that survive are often susceptible to accelerated arteriosclerosis. Treatment options for vein graft disease are currently limited. Angioplasty is frequently performed, though the long-term benefits have been disappointing. These and other drawbacks limit the clinical efficacy of SVG. For example, in the first post-operative month, about 8-12% of SVG occlude. One and 10-year occlusion rates approach about 20% and about 60% respectively, whereas the 10-year occlusion rate of IMA grafts is less than about 10%. This disparity has profound clinical implications. That is, patients who receive IMA grafts survive longer and suffer significantly less angina than patients who receive only SVG.

There is a recognized need to address these problems especially by preventing or treating vein graft disease in patients who have had or will undergo a bypass operation. See Mann et al. (1995) *PNAS (USA)* 92: 4502. Without wishing to be bound to theory, it is believed that thrombin, generated on the lumenal surface of implanted autologous venous grafts, mediates acute graft failure due to thrombosis as well as late failure due to neointimal hyperplasia and subsequent atherosclerosis. It is further believed that sustained local inhibition of thrombin and/or thrombin generation can improve long-term patency of human autologous venous grafts by preventing thrombosis and by resisting neointimal hyperplasia and atherosclerosis.

There is also a need to understand why many SVG fail with graft age. Acute graft occlusion (<1 month) has been reported to be nearly always due to thrombosis while subacute graft failure (<1 year) is thought to result from neointimal hyperplasia with superimposed thrombosis. Late graft failure (>1 to 5 years) has been disclosed as being caused by accelerated atherosclerosis that develops within the neointima. Without wishing to be bound by any theory, it is believed that thrombin is implicated in the pathogenesis of all three phases of SVG failure. More specifically, it is believed that injury to the graft endothelium occurs during implantation and in response to the sudden exposure to arterial pressure and shear stress. Injured endothelium is less thromboresistant due to a reduced capacity to generate tissue plasminogen activator, nitric oxide, prostacyclin, protein C and nascent expression of tissue factor. Thrombin, activated on the graft lumenal surface, is believed to impact fibrinogen cleavage and proteolytically activates platelet thrombin receptors, further stimulating their activation, adhesion and aggregation. A result is believed to be a favorable milieu for thrombosis, especially under conditions of sluggish blood flow.

The present invention addresses these and other problems eg., by providing therapeutic methods and engineered blood vessels that improve long-term patency of human autologous vein grafts and particularly SVG. With respect to SVG, practice of the invention can reduce or eliminate blood flow obstructing occlusions that typify standard bypass operations and often result in unwanted thrombosis, neointima hyperplasia and arteriosclerosis.

Therapeutic methods of the invention generally include introducing an effective amount of at least one nucleic acid encoding at least one agent that increases APC in cells of a subject blood vascular graft expressing the agent in the cells; and increasing the APC sufficient to treat the blood vessel. By the phrase "effective amount" or like phrase including "therapeutically effective amount" is meant at least about 20%, preferably between from about 50% to about 100%, more preferably at least about 200%, 300%, 500%, 1000%, 10,000% or more APC when compared to a non-treated (control) vessel as determined by the standard activated protein C assay.

Preferred invention practice involves mammals in need of such treatment eg., rodents such as rats, mice, as well as pigs, rabbits and primates. Preferred primates include human patients. More typical patients include individuals suffering from or susceptible to vascular graft failure, particularly the early and/or late failure associated with many SVG grafting attempts. Immunological relationship between the donor of the blood vessel and recipient of the graft can be allogenic, autologous, xenogeneic, or synthetic as needed. In preferred invention embodiments, the donor and recipient will be genetically identical and usually will be the same individual (syngeneic). In this instance, the blood vessel graft will be syngeneic.

In a preferred embodiment, TM is at least one of the agents used to increase the APC enzyme. Mature TM has been disclosed as being a major contributor to vascular thromboresistance. The protein has been reported to be about a 557 amino acid trans-membrane protein produced mainly by vascular and lymphatic endothelial cells but also by synovial cells, blood leukocytes and platelets. TM has been reported to bind activated thrombin in a 1:1 complex (Kd=2-3 nM) and alters its active site specificity such that thrombin is no longer able to cleave fibrinogen or the thrombin receptor but is able to activate protein C with high affinity (Km=0.5 µM). See Cadroy Y., et al. (1997) *Arterioscler Thromb Vasc Biol* 17:520; Wen, D., et al., (1987) *Biochemistry* 26:4350; Kurosawa, S., et al., (1988) *J. Biol. Chem* 263:5993; Zushi, et al., (1989) *J. Biol Chem.* 264: 10351; and Bourin, M. C. et al., (1986) *PNAS (USA)* 83:5924.

A wide variety of TM molecules suitable for use with this invention have been disclosed. See Majerus, P W. Et al. *J. Biol. Chem.*, (1984) 259; 12246, 1984; Aoki et al. *Thrombosis Res.* (1985) 37: 353; and Japanese Patent Application Kokai No. 60-199819). See also Maruyama et al. *J. Clin. Invest* (1985) 75:987; Suzuki et al. *J. Biochem.* (1988) 104: 628; WO 96/06933; U.S. Pat. Nos. 4,912,207; 5,695,964; Ohlin, A-K (1997) *Thromb. Haemost* 78: 396; and Wen D. Et al. (1987) *Biochemistry* 26: 4350 (disclosing eg., human TM cDNA).

A particular TM molecule in accord with the invention is the cDNA sequence encoding human thrombomodulin (hTM) as shown in U.S. Pat. No. 4,912,207 to Majerus; the disclosure of which is incorporated herein by reference. In particular, see FIG. 3 of the U.S. Pat. No. 4,912,207 (disclosing the cDNA and amino acid sequence of hTM). That sequence is reported to encode a protein having about 575 amino acids. Additionally preferred are functional fragments of the hTM cDNA sequence disclosed in the U.S. Pat. No. 4,912,207. By the phrase "functional fragment" as that term is used with reference to a TM encoding cDNA molecule is meant a nucleic acid fragment that encodes an amino sequence with at least about 85%, preferably at least about 95% of the activity of the thrombin binding activity of the full-length hTM sequence disclosed by the Majerus patent. Immunological methods for detecting binding between TM and thrombin are known in the field and have been reported. See eg., Waugh, J M et al. (1999) Circul. Res. 84: 84.

See also WO 96/06933 (also disclosing the hTM sequence).

Additionally preferred TM functional fragments have an open reading frame (ORF) sequence of between from about 1650 base pairs to about 1800 base pairs, preferably about 1700 to about 1750 base pairs as determined eg., by standard nucleic acid sequencing techniques.

Still further preferred TM molecules in accord with the invention include those nucleic acid sequences that hybridize under high stringency conditions to the full-length hTM sequence disclosed in the U.S. Pat. No. 4,912,207. By the phrase "high stringency" is meant at least one post-hybridization wash step using 6×SSC, 0.5% SDS, 100 microgram carrier DNA, and 50% formamide at about 42° C. See Sambrook et al. infra, for more information.

Other preferred TM molecules include nucleic acid sequences encoding allelic variants of the amino acid sequence disclosed in the U.S. Pat. No. 4,912,207 as full-length hTM. Also envisioned are TM molecules that encode amino acid sequences having at least one amino acid substitution, deletion (contiguous or non-contiguous) or addition to the full-length sequence reported by the U.S. Pat. No. 4,912,207. Preferably, such substitutions, deletions and additions involve between from about 1 to about 50 amino acids, more preferably about 1 to about 10 amino acids. Preferred amino substitutions include conservative substitutions. Accordingly, a tyrosine amino acid substituted with a phenylalanine will be an example of a conservative amino acid substitution, whereas an arginine replaced with an alanine would represent a non-conservative amino acid substitution.

Further preferred TM molecules in accord with the invention encode amino acid sequences that facilitate good TM and APC activity as determined by one or more of the following assays.

A preferred assay for detecting suitable TM molecules is the following assay referred to herein as a standard protein C assay or related phrase. Briefly, transduced rabbit vein segments are divided and placed into the bottom of a well so that the lumenal surface from the bottom of that well. The transduced vessels are then incubated with about 10 nm α-thrombin and about 1 µM protein C for about 20 minutes. Supernatants are subsequently removed and the amount of activated protein C (APC) is determined by measuring conversion of the chromogenic substrate S-2366. The rate and extent of protein C activation can be quantitated, if needed, by using a standard microplate reader with reference to a standard APC curve. See Example 3 for more information about this assay.

Another preferred assay for detecting TM activity is the standard rabbit vein graft assay described in Examples 1 and 2, below. Reference herein to a "standard rabbit vein graft assay" or related phrase refers to the model described in those examples. Briefly, practice of the model involves taking a segment of jugular vein and interposing it into the ipsilateral carotid arterial circulation in an end-to-side fashion. Immediately prior to implantation, the vein graft segments are preferably transduced ex vivo with at least one suitable viral vector encoding TM (or functional fragment thereof). TM expression is detected and quantified, if desired, by performing a TM immunoassay using a suitable anti-TM antibody. TM expression can be monitored as needed in the assay e.g, up to about one to six months, preferably about two to about 60 days, more preferably about three days to about 50 days. See Examples 1 and 2 below for additional information.

As discussed, it is believed that loss of TM from the lumenal surface of vein grafts significantly contributes to local thrombin generation and subsequent thrombin-mediated graft failure. The invention provides useful methods to prevent or replace the TM loss, thereby decreasing local thrombin generation and subsequent graft failure. The expression pattern of thrombomodulin in human saphenous vein grafts, the impact on local thromboresistance and the effect of viral vector-mediated expression of thrombomodulin on graft thromboresistance and development of accelerated atherosclerosis. See the Examples below.

As also discussed, the invention is flexible and is fully compatible with other agents for increasing APC. Illustrative of such agents is human endothelial cell protein C receptor (EPCR) including functional fragments thereof. The receptor is reported to be a 235 amino acid endothelial cell-specific trans-membrane protein that binds protein C. It is thought to bind protein C (Kd=30 nM) and "present" it to the thrombin/TM complex, thus augmenting the rate of protein C activation. EPCR is expressed predominantly by the endothelium of large arteries and veins. The in vivo regulation of EPCR activity is not as well defined as it is for TM. Like TM, the EPCR gene is down-regulated by exposure to inflammatory cytokines such as TNF-α.

A preferred EPCR sequence is the full-length human EPCR sequence disclosed eg., in U.S. Pat. Nos. 5,852,171 and 5,804,392; the discloses of which patents are incorporated herein by reference.

See also Fukudome and Esmon, 1994 J. Biol. Chem 269: 26486; Fukudome, et al. 1996. J. Biol. Chem. 271:17491; Regan, et al. 1996. J. Biol. Chem. 271:17499; and Esmon C T (2000) Thromb Haemost 83:639 (disclosing additionally preferred EPCR sequences).

A particular EPCR molecule in accord with the invention is the cDNA sequence encoding human EPCR as shown in U.S. Pat. No. 5,852,171 as SEQ ID No: 1. The amino acid sequence encoded by that cDNA is shown in the U.S. Pat. No. 5,852,171 as SEQ ID NO: 2. Additionally preferred are functional fragments of the nucleic acid sequence shown as SEQ ID NO: 1 in the U.S. Pat. No. 5,852,171. By the phrase "functional fragment" as that term is used with reference to a EPCR encoding DNA molecule is meant a nucleic acid fragment that encodes an amino sequence with at least about 85%, preferably at least about 95% of the protein C (PC) activation when compared to the full-length human EPCR cDNA sequence disclosed as SEQ ID NO: 1 in the U.S. Pat. No. 5,852,171. Methods for detecting and quantifying PC activation by EPCR have been reported. See Esmon C T (2000), supra; Fukudome, supra.

Additionally preferred EPCR functional fragments have an open reading frame (ORF) sequence of between from about 1200 to about 1400 base pairs, preferably about 1250 to about 1350 base pairs as determined eg., by standard nucleic acid sequencing techniques.

Still further preferred EPCR molecules in accord with the invention include those nucleic acid sequences that hybridize under high stringency conditions to the full-length cDNA sequence disclosed as SEQ ID NO: 1 in the U.S. Pat. No. 5,852,171.

Other preferred EPCR molecules include nucleic acid sequences encoding allelic variants of the amino acid sequence disclosed in the U.S. Pat. No. 5,852,171 as full-length human EPCR (SEQ ID NO:2). Also envisioned are EPCR molecules that encode amino acid sequences having at least one amino acid substitution, deletion (contiguous or non-contiguous) or addition to the full-length sequence reported by the U.S. Pat. No. 5,852,171. Preferably, such substitutions, deletions and additions involve between from about 1 to about 50 amino acids, more preferably about 1 to about 10 amino acids. Preferred amino substitutions include conservative substitutions.

Further preferred EPCR molecules in accord with the invention encode amino acid sequences that facilitate good activation of PC as determined by the standard protein C assay. Preferably, such molecules encode amino acid sequences that provide for at least about an 80% increase in protein C activation in the standard protein C assay compared to a control blood vessel graft, preferably between from about 90% to about a 100% increase.

See also WO0010609, PCT/US95/09636, EP0937104 and U.S. Pat. Nos. 5,804,392, 6,200,751 (disclosing additionally preferred EPCR sequences).

Accordingly, routine testing, eg., using the standard assays described below, can readily identify one or a combination of acceptable agents for increasing APC of subject vascular grafts.

Additionally preferred agents for increasing APC include certain cell factors that are known to modulate immune and inflammatory responses in vivo. Because inflammation is known to reduce the expression of TM, inhibition of inflammatory pathways can result in preserved TM expression and APC generation. Particularly preferred are cell factors that interact, either directly or indirectly, to reduce or completely block activity of the transcription factor, NF-κB. See Brockman et al. (1995) *Mol. Cell. Biol.* 15: 2809. It has been demonstrated in vitro that inhibition of NF-κB can prevent TM down-regulation in response to exposure to the inflammatory cytokine TNF-α. See Example 12.

More preferred agents include dominant negative mutants of a family of inhibitory proteins called "IκB". It has been reported that IκB interacts with NF-κB and blocks activity of the transcription factor. As shown below in Example 12, transduction of cultured cells with an adenovirus vector expressing the IκB factor prevented unwanted TM down-regulation in response to TNF-α stimulation. See also FIG. 12.

By the term "functional fragment" of the IκB factor is meant a fragment having at least about 90%, preferably at least about 95% of the activity of full-length IκB as determined by the IκB activity assay disclosed by Brockman et al. (1995) *Mol. Cell. Biol.* 15: 2809.

Preferred methods of the invention employ a suitable into which at least one nucleic acid encoding the agent for increasing APC has been inserted. Particular vectors of interest include viral vectors including specific RNA and DNA viral vectors. Retroviral vectors include moloney murine leukemia viruses. DNA viral vectors are preferred. These vectors predominantly include adenovirus vectors, adeno-associated virus vectors, pox vectors such as orthopox or avipox vectors, herpes virus vectors such as a herpes simplex I virus (HSV) vector. See A. I. Geller et al., *J. Neurochem*, 64:487 (1995); F. Lim et al., in *DNA Cloning: Mammalian Systems*, D. Glover, Ed. (Oxford Univ. Press, Oxford England) (1995); A. I. Geller et al., *Proc Natl. Acad. Sci.:* U.S.A.:90 7603 (1993); A. I. Geller et al., *Proc Natl. Acad. Sci USA*: 87:1149 (1990). For disclosure relating to useful adenovirus vectors, see LeGal LaSalle et al., *Science*, 259:988 (1993); Davidson, et al., Nat. Genet., 3:219 (1993); and Yang et al., *J. Virol.*, 69: 2004 (1995). See Kaplitt, M. G., et al., *Nat. Genet.*, 8:148 (1994) and references cited therein for information about adenovirus-associated vectors.

Adenovirus vectors mediate relatively short (about 1-3 weeks), but efficient and robust, transgene expression in transduced target cells. Retrovirus vectors, though suited ideally for ex vivo gene transfer, can mediate long term (months to years) transgene expression due to viral integration into the host genome. Adeno-associated virus vectors have the advantage of efficient transduction in vivo as well as the potential for long term transgene expression (months) due to viral integration into the host genome The particular vector chosen will depend upon the target cell and the condition being treated. The introduction can be by standard techniques, e.g. infection, transfection, transduction or transformation. Examples of modes of gene transfer include e.g., naked DNA, $Ca_3(PO_4)_2$ precipitation, DEAE dextran, electroporation, protoplast fusion, lipofecton, cell microinjection, and viral vectors.

It is believed that amino acid sequences expressed by such vectors are often present for much longer times eg., a few days up to a few weeks or more. This feature can usefully extend the beneficial effects of many agents when used to improve vascular graft patency.

Vectors derived from adenoviruses ie., viruses causing upper respiratory tract disease and also present in latent primate infections, are generally known and are preferably used in accord with this invention. Importantly, the ability of many adenoviruses to attach to cells at low ambient temperatures is one advantage in transplant settings. This advantage can facilitate gene transfer during reduced temperature storage of subject vessels. Such viruses can be manipulated in one or a combination of ways to effect expression of the desired agent for increasing protein C activity. Preferably, a recombinant adeno-associated virus (AAV) vector is used to express same. In such vectors, the nucleic acid encoding the agent including preferred TM and EPCR molecules, may be under the control of one or more different constitutive or regulable promoters.

A preferred adenovirus vector construct for use with the invention includes an expression cassette comprising at least one, preferably one or two nucleic acid sequences that encode agent for increasing protein C activity. For example, the agent encoded by the vector can be TM DNA in operative association with one or more constitutive or regulable promoters. In this example, subject vessel grafts will generally be transduced with at least one other vector in which the agent encoded by the vector is EPCR DNA in operative association with the same or different promoters. Alternatively, the EPCR and TM DNA can be provided in the same vector. Further preferred adenovirus vectors typically include a poly A sequence downstream therefrom.

Examples of particular adeno-associated viruses (AAV) and suitable vectors derived therefrom have been reported in U.S. Pat. No. 6,156,303, the disclosure of which has been incorporated by reference.

Illustrative promoters include the known cytomeglovirus (CMV) promoter/enhancer and the Rous sarcoma virus long terminal repeat (RSV) promoter. Other promoters suitable for use include U1 small nuclear RNA promoter, and ICAM-2 promoter. See the Examples section for more information.

The expression cassette of preferred adenovirus vectors is typically introduced into the adenovirus genome by recombination between two plasmids in a suitable cell line (eg., 293) that can provide viral function, preferably E1 gene function in trans to allow replication of the virus which lacks E1.

In general, preparation of vectors of the invention can be accomplished by procedures disclosed herein and by recognized recombinant DNA techniques, e.g. preparation of plasmid DNA, cleavage of DNA with restriction enzymes, ligation of DNA, transformation or transfection of a host, culturing of the host, and isolation and purification of the desired vector construct. Such procedures are generally known and disclosed e.g. in Sambrook et al., *Molecular Cloning* (2d ed. 1989); and Ausubel et al., *Current Protocols in Molecular Biology*, John Wiley & Sons, New York, 1989; the disclosures of which are herein incorporated by reference.

More specific disclosure relating to making adenovirus vectors via cre-lox recombination methods can be found in Hardy, S. et al. (1997) *J. Virol.* 71: 1842. See also FIGS. 7A-B (showing in schematic form construction of adenovirus vectors that encode hTM or β-galactosidase). See also Rade, J J et al. (1996), supra, for additional information relating to making and using vector constructs.

Disclosure relating to the blood coagulation cascade can be found in R. Hoffman et al., *Hematology: Basic Principles and Practice*, New York: Churchill Livingston, Inc., 1991; C. Kjeldsberg et al., *Practical Diagnosis of Hematologic Disorders*, Chicago: American Society of Clinical Pathologists Press, 1989. See also Esmon, C. T., (2000), supra as well as references cited therein for a discussion of the role of the TM and EPCR proteins in the cascade.

Without wishing to be bound to theory, it is believed that alterations in the expression and activity of TM and EPCR by vascular endothelial cells play prominent roles in the pathophysiology of both early and late SVG failure. It is particularly believed that vein graft "arterialization" decreases local APC generation due to a loss of TM expression. Cook examined TM activity on human SVG segments prepared during coronary artery bypass surgery. The process of SVG harvesting and short-term storage in heparinized saline, as would normally be done during the surgical procedure, resulted in a 28% reduction in protein C activation compared to unmanipulated vein segments. It is further believed that exposure to arterial shear stress may down-regulate TM gene expression. Gosling demonstrated that placement of human saphenous vein endothelial cells under arterial flow conditions for 90 minutes caused a 40% decrease in surface TM expression as determined by quantitative immunohistochemical staining. It is further believed that there is a marked inflammation in grafts shortly after implantation. Inflammatory cells adherent to the graft lumen release cytokines may also be a stimulus for down-regulation of TM and EPCR gene expression. Inflammatory cells also express abundant amounts of tissue factor, thus producing a local procoagulant milieu. It is also believed that restoration of protein C activation can limit neointimal hyperplasia. Waugh recently demonstrated that adenoviral-mediated gene transfer of TM to balloon-injured rabbit femoral arteries reduced the intima/media ratio by 38%. See Nwasokwa On. *Ann Int Med.* (1995) 123: 528; Channon K. M. et al. *Arterioscler Thromb Vasc Biol.* (1997) 17:1313; Cook J M et al. (1991) *J. Vasc. Surg.* 14: 147; and Gosling M. (1999) *Circulation* 99: 1047.

The neointima of blood vessels has attracted attention. Work has revealed that it differs phenotypically from both the endothelium and quiescent media of a normal artery and is a more avid substrate for the development of atherosclerosis. Neointimal SMC express adhesion molecules and secrete cytokines that are chemoattractants for circulating monocytes. Ingress of monocytes with subsequent uptake of oxidized-LDL leads to the formation of foam cells, which can be identified in over 50% of grafts 1 to 15 years of age. As with native vessels, the atheromata found in SVG are prone to rupture causing acute coronary syndromes. 44% of SVG excised 5 to 10 years after implantation contain ruptured plaques with superimposed thrombi. See Mann, M. et al. (1995) *PNAS (USA)* 92: 4502.

The present addresses these problems and provides experimental evidence that implantation of venous endothelial cells into the arterial circulation alters TM and EPCR expression resulting in a diminished capacity to activate protein C. Impaired protein C activation, in concert with enhanced local tissue factor expression, facilitates local thrombin generation which promotes SVG failure, acutely because of thrombosis and chronically because of thrombin-induced neointimal hyperplasia and subsequent accelerated atherosclerosis. It is believed that preventing the loss of at least one of TM and EPCR, preferably both of same via viral-mediated gene transfer will help restore thromboresistance and prevent SVG failure.

Preferred invention methods increase protein C activation of the treated blood vessel (graft) at least about one order of magnitude higher than a control vessel as determined by the standard assay. Also preferred is increased protein C activation of the treated blood vessel (graft) is detectable for at least about one to two days, preferably at least about a week or more.

In one invention embodiment, administration of TM and EPCR agents is preferred to prevent or treat blood vessel graft failure. As discussed, TM and EPCR are thought to be potent anticoagulant molecules found normally on the lining of blood vessels. These proteins are also thought to help keep the blood that circulates through the blood vessels from clotting. As discussed in the Examples below, it has been found that the amount of TM normally found in veins is dramatically reduced when they are used for bypass surgery. It is also believed that the amount of TM and/or EPCR is reduced, thereby pre-disposing vein grafts to fail. Blood clot formation and accelerated arteriosclerosis is promoted in these vein grafts.

The present disclosure illustrates the foregoing particular problems by demonstrating a decrease in TM and EPCR expression in a rabbit model of human vein graft disease (referred to herein as a the standard rabbit vein graft assay). The therapeutic methods of the invention address the problem, in one aspect, by increasing expression of at least one of TM and EPCR, preferably both of the proteins, using a gene therapy approach. Preferred methods restore activity of the proteins and prevent or reduce the severity of vein graft failure by preventing early clotting and development of accelerated arteriosclerosis. See the Examples below (showing eg., that effective thrombin inhibition diminishes neointimal hyperplasia following vessel damage).

The present invention addresses the following specific objectives.

First, it discloses TM expression by human saphenous vein grafts in autopsy tissue library. Immunohistochemical methods are employed to determine the degree and location (i.e. vascular layer and cell type) of thrombomodulin protein expression, its relationship to tissue factor expression, and correlation to age. Second, it examines expression of TM over time by human saphenous vein grafts placed in organ culture. More specifically, it reports the relationship of thrombomodulin expression to that of tissue factor, the development of neointimal hyperplasia and to thromboresistance of the lumenal endothelium using an in situ coagulation assay. Third, the invention disclosure reports on transduction of human saphenous vein grafts with a recombinant adenoviral viral vector expressing human thrombomodulin. A goal is to determine the effects on lumenal thromboresistance and thrombin-induced neointimal hyperplasia. It is possible to determine if TM over-expression in this ex vivo model is able to modulate medial smooth muscle cell proliferation, migration and/or matrix secretion.

Still other invention objectives include reporting the expression pattern of TM and EPCR in a rabbit model of autologous vein graft disease, the consequent effects on local thromboresistance and the effects of viral vector-mediated restoration of protein C activity on early and late graft failure. Particularly, the disclosure shows 1) quantitation of the in vivo expression of the EPCR protein using computerized quantitative immunohistochemical analysis and to determine the expression patterns of the TM and EPCR genes using quantitative RT-PCR in autologous rabbit vein grafts; 2) a determination of the time-course of inflammation in rabbit vein grafts and to establish a correlation with the alterations in TM and EPCR expression; 3) construction of a series of adenoviral vectors expressing both TM and EPCR in combination and under the control of various promoters in order to optimize protein C activation by transduced endothelial cells in vitro; and 3) determination of the effect of adenovirus vector-mediated expression of TM and EPCR on the restoration of thromboresistance, degree of inflammation and the development of neointimal hyperplasia in rabbit vein grafts.

The methods disclosed herein can be employed as the sole treatment protocol ie., to prevent or treat blood vessel particularly against failure when grafted into a host recipient. However in one embodiment, the invention can be used as adjunctive therapy to augment a standard anticoagulant or antiplatelet administration. Such protocols include the routine administration of therapeutic amount of at least one of an anticoagulant, antiplatelet, antithrombotic, or thrombolytic drug to treat or prevent vascular graft disease. Examples of such standard treatment protocols include, but are not limited to, therapeutic administration of aspirin, clopidogrel, ticlopidine, dipyridamole, coumadin, including acceptable derivatives thereof. See A. G. Gilman et al., *The Pharmacological Basis of Therapeutics*, 9$^{th}$ Ed. McGraw-Hill Inc. New York (disclosing recognized anti-clotting protocols using a variety of suitable drugs).

The invention can be practiced before, during, or after a particular anticoagulant or antiplatelet protocol as needed. More specifically, administration of one or more of the anticoagulant, antiplatelet, antithrombotic, thrombolytic, or other drugs of choice can be conducted before, during, or following practice of the invention methods. For preferred administration routes, see *Remington's Pharmaceutical Sciences* (Mack Pub. Co., Easton, Pa., 1980). In one embodiment, the method for treating blood vessels is adapted so that the nucleic acid encodes at least one other of such drugs, preferably an anticoagulant molecule, more preferably hirudin. In another invention embodiment, the anti-coagulant, analgesic, antithrombotic, thrombolytic, or other drug is administered step a) or after step c) of the method.

It will be appreciated that actual preferred vascular graft treatment methods according to the invention will vary in line with recognized parameters including the particular agent chosen (eg., TM, EPCR or both), the particular vessels used, and also the vector selected. Additional parameters include the mode of application and grafting, the particular site of administration of the graft, the patient's weight, general health, sex, etc., the particular indication being treated, etc. and other such factors that are recognized by those skilled in the art including the attendant physician or veterinarian. Optimal administration rates for a given protocol of administration can be readily determined by those skilled in the art using conventional dosage determination tests.

By the phrase "standard thrombomodulin detection assay" is meant the assay described in Example 2, for instance. Briefly, graft sections are prepared and contacted with a suitable anti-TM polyclonal antibody for TM staining. TM expression is detected and preferably quantitated using digital threshold analysis. To control for cell loss, sections are also stained for von Willibrand factor (vWF). Methods for performing antibody staining are generally described in Ausubel et al., supra.

By the phrase "standard atherosclerotic rabbit vein graft model" is meant the model described in Example 13, for instance. Generally, the model involves performing the rabbit vein graft model described in Example 1 on specific rabbits pre-disposed to develop atherosclerosis. Grafts are manipulated and harvested as described. Lipid-laden macrophages (foam cells) can be detected and preferably counted by inspection. Typically, presence of significant foam cells in grafts (when compared to suitable control grafts) is indicative of accelerated atherosclerosis.

By the term "artificial graft" is meant a synthetic or semi-synthetic vascular material seeded with naturally-occuring or recombinantly manipulated endothelial cells. Methods for harvesting and manipulating endothelial cells have been described. See eg., WO 97/30083, WO 93/13807, Lundell, A. et al. (1999) *Circulation* 100: 2018, J J. Rade, supra, J J. Rade (1999) *Gene Therapy* 6: 385. More specific examples of such grafts include those made (whole or in part) from synthetic fibers such as Dacron, Teflon, Gore-Tex (including combinations thereof). Preferred artificial grafts of the invention are made whole or in part from Dacron, Teflon, or Gore-Tex and include seeded endothelial cells transduced to express at least one agent as defined herein. Preferred agents include human Tm, human EPCR; including functional fragments thereof.

The following non-limiting examples are illustrative of the invention.

EXAMPLE 1

Standard Rabbit Vein Graft Model

The well-characterized rabbit vein graft model referred to previously is described in this example. The model can be used to study the pathobiology of vein graft failure and the effects of viral-mediated gene transfer on graft thromboresistance, neointimal hyperplasia and development of atherosclerosis. Further, it is representative of related human pathologies. In general, the model is made by interposing a segment of jugular vein into the ipsilateral carotid arterial circulation in an end-to-side fashion. Immediately prior to implantation, the vein graft segments can be transduced with at least one suitable viral vector according to the invention.

A. Surgical Techniques—Practice of the model involves use Pasteurella-free male New Zealand White rabbits weighing 2.5-3.5 kg. All control and experimental groups were limited to the minimum number necessary to achieve statistical significance plus 15% to account for post-operative deaths and graft thrombosis (loss rate in our laboratory).

The procedure was performed in an operating suite using sterile instruments and technique. Anesthesia was induced with xylazine (7 mg/kg) end ketamine (35 mg/kg) IV via ear vein then maintained on Halothane (0.5-1.0%) inhalational anesthetic following endotracheal intubation. During surgery the heart rate and cardiac rhythm were continuously monitored. The animals were prepped and draped in sterile fashion and a midline neck incision made to expose the left carotid artery and jugular vein. A 3 cm segment of jugular vein was isolated and the distal stump ligated. The proximal stump was canulated, washed, then filled with 200:1 of M-199 media containing the appropriate dose of virus or M-199 media alone (control). Following a one hour incubation, the vein segment was washed with M-199 media, removed from the animal and placed in sterile saline. The ipsilateral carotid artery was then isolated and the animal given 300 U of heparin sulfate intravenously. The vein segment was then anastomosed to a divided carotid artery in end-to-side fashion using 8-O polypropylene sutures placed with aide of an operating microscope. (FIG. 1). Topical papeverine was applied to prevent spasm and the wound closed with 3-O subcutaneous sutures and skin staples. The animal was extubated in the operating suite and recovered for a period of at least 24 hours in the Cardiac Surgery Animal Laboratory before being returned to the animal holding facility.

Post-operative analgesia (buprenorphine, 0.01-0.05 mg/kg subcutaneously every 12 hours) was given routinely for the first 24 hours, longer if the animal appears to be in pain. In our experience, rabbits recover quickly within hours of the surgery and generally are without significant pain. Animals that do not recover quickly from the surgery (within the first 24 hours) are usually systemically ill (e.g from pneumonia) and are euthanized.

At the time of graft harvest, the rabbits were anesthestized and re-intubated as above. Following harvesting of the graft the animals are euthanized using an overdose of potassium chloride. In addition, any animal in distress will be euthanized an overdose of pentobarbital (50 mg/kg).

B—Results Rabbit jugular vein segments exhibit partial endothelial denudation with fibrin deposition and platelet adhesion as quickly as 1 hour following implantation into the carotid circulation. Within the first two weeks after grafting, endothelial regeneration is complete and the neointima has begun to form. SMC proliferation indices peak at 1 week after implantation, decrease substantially within 2 to 4 weeks and return to near quiescent levels by 12 weeks. After significant SMC proliferation has ceased (by 4 weeks) matrix deposition continues, increasing neointimal mass for up to 12 weeks. At full maturation, the graft wall thickness has increased nearly 10-fold, most of which is due to neointimal hyperplasia.

Figure 2B:
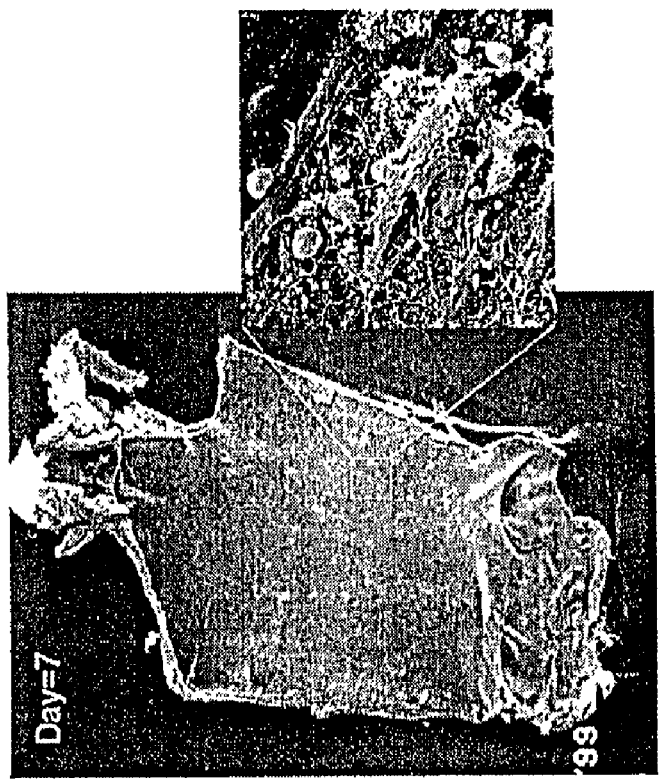
FIGS. 2A-B are scanning electron micrographs showing lumenal surfaces of rabbit vein grafts harvested 1 day (FIG. 2A) and 7 days (FIG. 2B) after implantation.
Figure 2A:
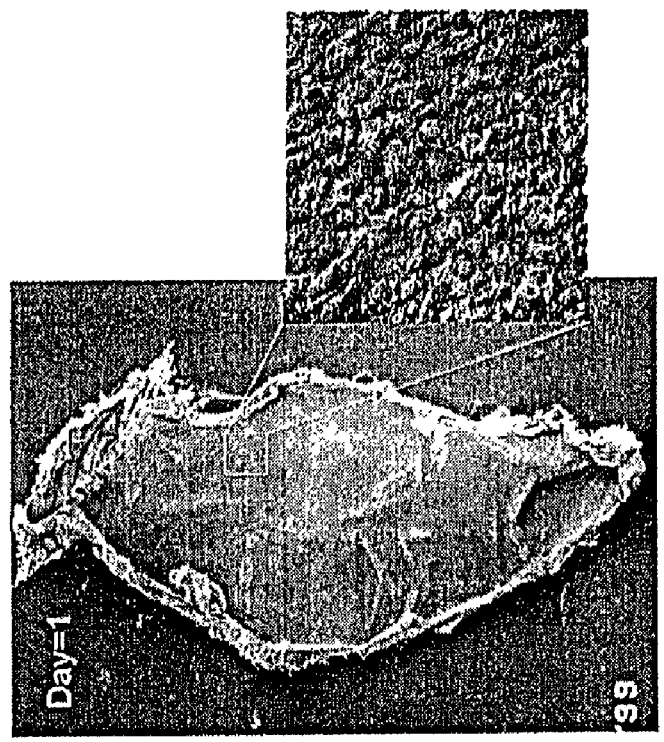

Davies used light and electron microscopy to demonstrate that within hours of implantation the endothelium becomes stretched and begins to retract, though there is little endothelial cell loss per se. See Davies, M G. (1993) *Eur. J. Vasc. Surg.* 7: 156. Over the ensuing days, inflammatory cells can be seen adhering to the lumenal surface and migrating into the edematous subintimal layers. We have also noted this in grafts prepared according to this example using scanning electron microscopy (FIGS. 2A and 2B). By day 14, endothelial regeneration is nearly complete. Zwolak meticulously characterized the contribution of SMC proliferation to vessel remodeling: SMC proliferation indices peak at 1 week after implantation, decrease substantially within 2 to 4 weeks and return to near quiescent levels by 12 weeks. After significant SMC proliferation has ceased (by 4 weeks) matrix deposition continues, increasing neointimal mass for up to 12 weeks. At full maturation, the graft wall thickness has increased nearly 10-fold, most of which is due to neointimal hyperplasia. If the animals are fed a high cholesterol diet, the neointima exhibits the changes of early atherosclerosis with marked foam cell infiltration.

FIGS. 2A-B are more specifically explained as follows. The figures show scanning electron micrographs of the lumenal surface of rabbit vein grafts harvested 1 day (FIG. 2A) and 7 days (FIG. 2B) after implantation. Note the preserved endothelial cell integrity, the leukocyte adhesion and the platelet and fibrin deposition at day 7.

EXAMPLE 2

Thrombomodulin (TM) Expression in Vein Grafts

Figure 3:
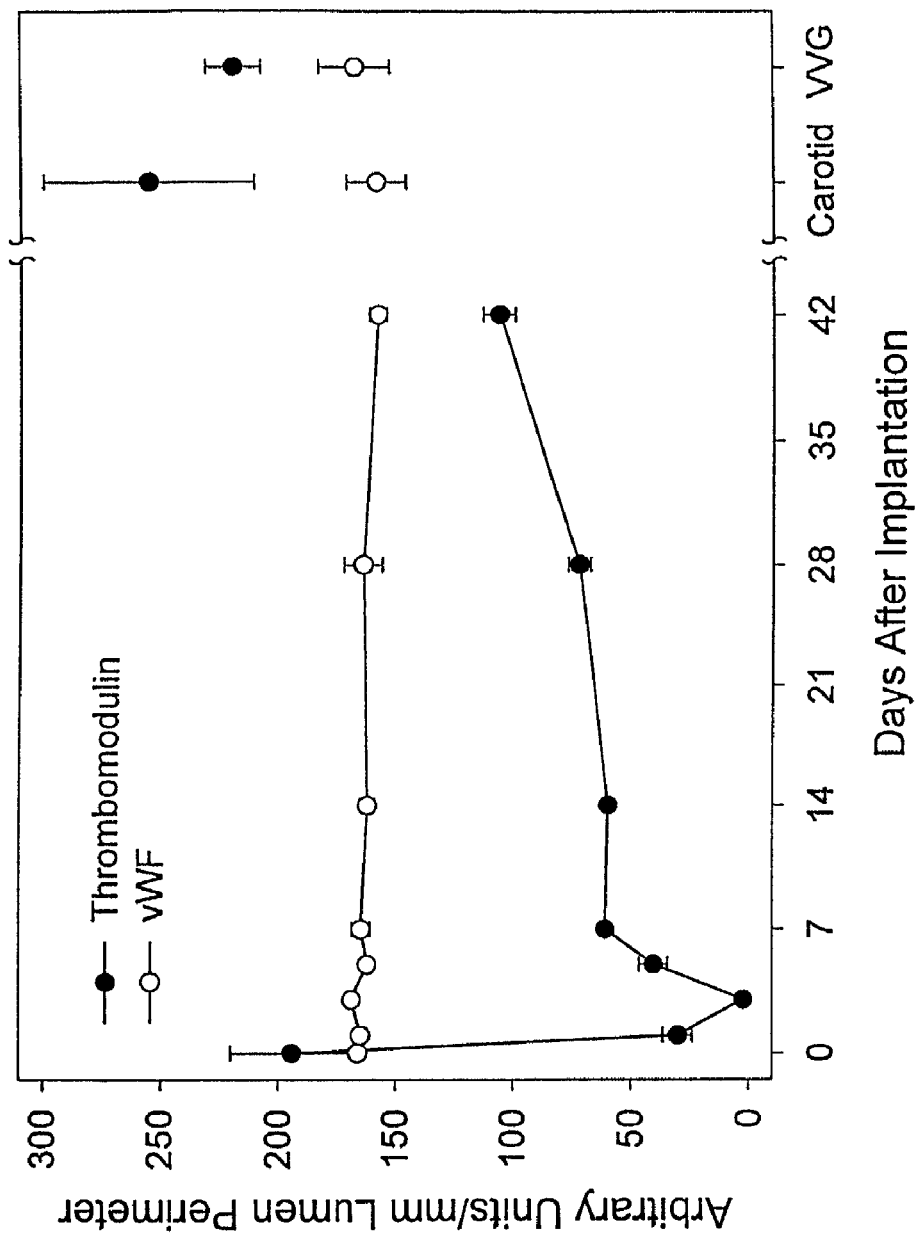
FIG. 3 is a graph showing TM protein expression in vein grafts as a function of implantation time.
Figure 4:
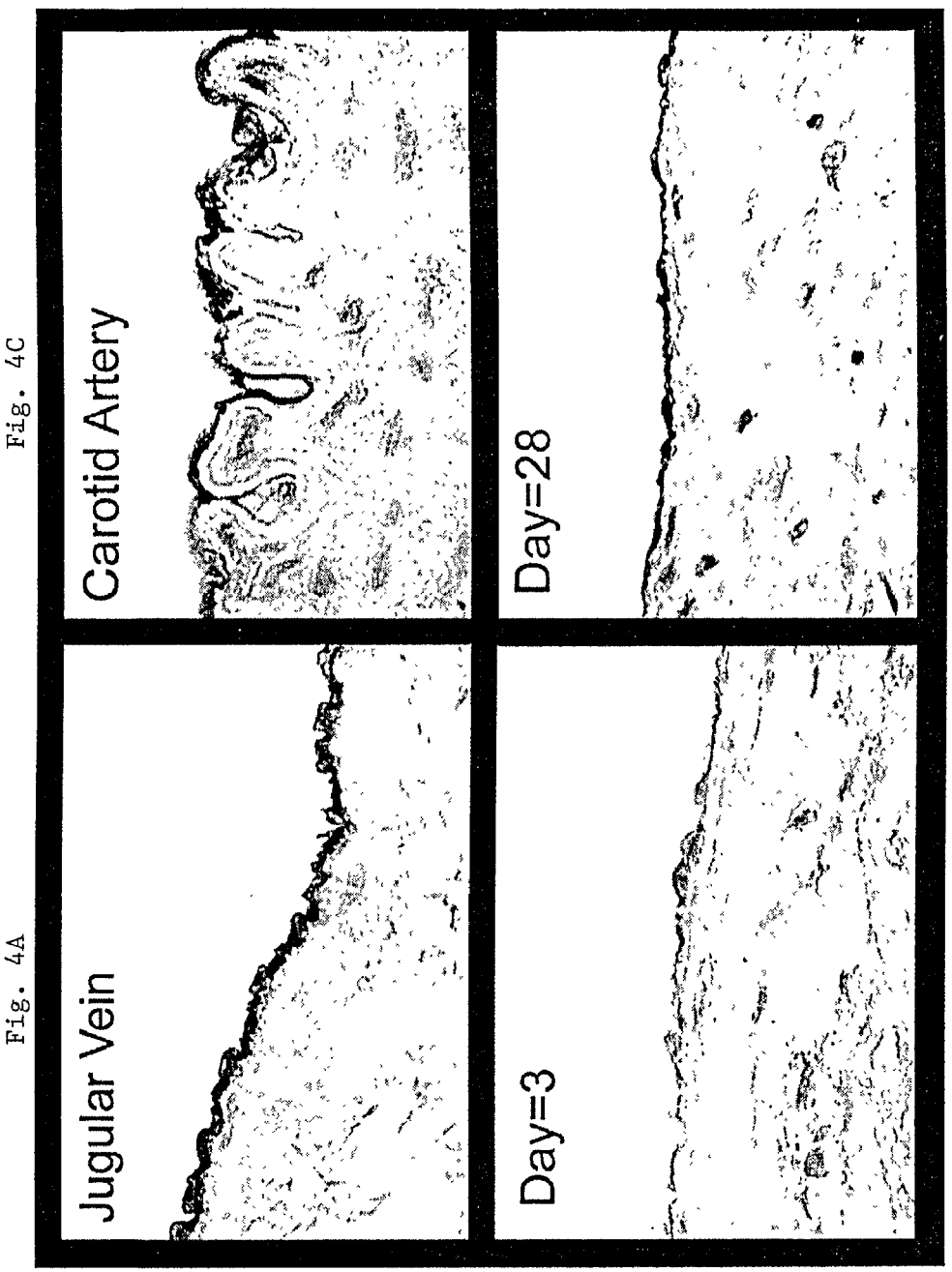
FIGS. 4A-D are photographs showing thrombomodulin (TM) expression in rabbit jugular and carotid arteries. Jugular vein grafts were harvested at day 3 (FIG. 4B). Carotid artery was harvested at day 28 (FIG. 4D). To control for endothelial cell loss, sections were stained for von Willibrand factor (vWF) (FIGS. 4A and 4C).

The rabbit vein graft model was performed along lines described above in Example 1. TM expression was determined in the vein grafts using immunochistochemical analysis. FIG. 3 shows representative sections of normal rabbit jugular vein (day=0 graft) and grafts harvested 3 and 42 days after implantation and stained for TM using a specific anti-rabbit TM polyclonal antibody (American Diagnostica Inc.). TM expression was found to decrease dramatically in rabbit vein grafts shortly after implantation and to exhibit a partial recovery by day 42. To more completely quantify alterations in TM expression, rabbit vein grafts harvested at intermediate time points were stained for TM and the amount of TM expression quantified using digital threshold analysis. To control for endothelial cell loss, adjacent sections were stained for von Willibrand factor (vWF) using a polyclonal anti-human vWF antibody (Sigma) and analyzed in similar fashion (FIG. 3) 28 days. TM expression was found to fall by 98% in day 3 grafts compared to normal jugular veins (day=0 grafts). By day 42, TM expression had partially recovered but was only 55% and 42% compared to jugular vein and carotid artery controls, respectively. Vein grafts reimplanted into the venous circulation (VVG) demonstrated no decrease in TM staining, suggesting that the surgical procedure itself had no significant effect on TM expression. Staining for vWF was consistent at all time points and comparable to vein and artery controls, suggesting that the decrease in TM expression was not due to endothelial cell loss.

These results suggest that implantation of vein grafts into the arterial circulation reduces TM expression that results in impaired graft thromboresistance. Diminished thromboresistance facilitates local thrombin generation that promotes SVG failure, acutely because of thrombosis and chronically because acceleration of-atherosclerosis. Prevention of TM loss, by gene transfer techniques, will restore thromboresistance and prevent SVG failure.

FIGS. 4A-D show native rabbit thrombomodulin and von Willibrand factor protein expression in rabbit vein grafts. FIG. 3 quantifies such expression using digital threshold analysis. Data is the mean of n=3–6+/−SD vessels per time point and expressed as arbitrary units (AU) per length of lumen perimeter.

EXAMPLE 3

Relationship between the Capacity of Rabbit Vein Grafts to Activate Protein C and Local Thrombin Activation Unopposed local thrombin activation is a proximate cause of early vein graft failure. In a normal blood vessel, small amounts of thrombin are continually generated. TM, present on the endothelial cell surface in large quantity, binds thrombin and converts its active site specificity from a procoagulant to an anticoagulant molecule via activation of protein C. Activated protein C (APC), along with its co-factor protein S, degrades the clotting factors Va and VIIIa thereby potently inhibiting further thrombin generation. Loss of TM expression would be expected to result in a reduced capacity of the graft endothelium to generate protein C with subsequent facilitation of local thrombin generation.

Figure 5:
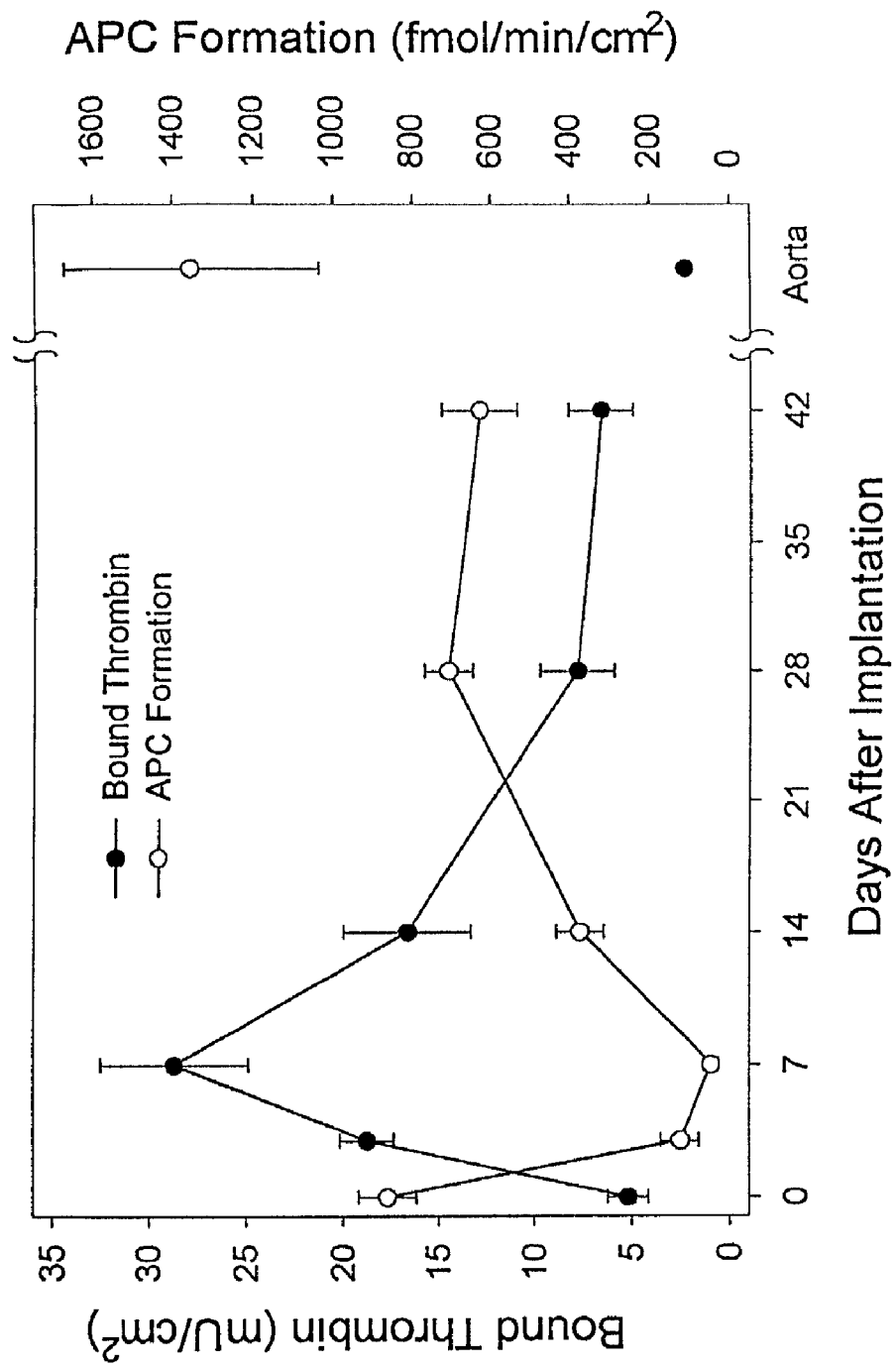
FIG. 5 is a graph showing levels of bound thrombin and APC formation as a function of implantation time.

To determine the consequences of decreased TM expression on graft thromboresistance, we measured both the capacity of the graft endothelium to activate protein C and the amount of thrombin activity bound to the graft surface (a measurement of local thrombin activation). In this in situ assay, longitudinally divided vessel segments were placed into an acrylic template such the lumenal surface formed the bottom of a well with known surface area. Vessels were incubated with 10 nM α-thrombin and 1.0:M protein C for 20 minutes followed by the addition of excess hirudin. The supernatants were removed and the amount of activated protein C (APC) that was generated was determined by measuring conversion of the chromogenic substrate S-2366 (Chromogenix) in a Kinetic Microplate Reader (Molecular Devices) with comparison to an APC standard curve. As expected, the capacity of the graft to generate APC paralleled TM protein expression: By day 7, protein C activation was reduced by nearly 95% compared to control jugular veins and exhibited an incomplete recovery by 42 days (FIG. 5). As with TM protein expression, APC formation at 6 weeks remained significantly lower than aorta controls.

Bound thrombin activity on the graft surface was measured using the same acrylic template. Vessels were incubated with the relatively thrombin-specific chromogenic substrate S-2238 (Chromogenix) for 20 minutes at 37EC. The grafts were then washed with excess hirudin and incubated a second time with S-2238. The difference in the absorbance before and after hirudin treatment is conversion of the substrate attributable to bound thrombin activity. This is quantified by comparison to a thrombin standard curve. Bound thrombin activity was found to be inversely proportional to the capacity of the graft to generate APC (FIG. 5). Thrombin activity peaked at nearly 30 mU/cm2 on day 7, but remained elevated for 14-28 days. The degree of bound thrombin activity on day 7 is roughly similar to that found after acute balloon injury to a rabbit femoral artery but of significantly longer duration (Dryjksi et al. (1985) *Thromb Haemost*, 54:773 and Ghigliotti et al., (1998) *Arterioscler Thromb Vasc* 18:250).

FIG. 5 shows the inverse relationship between loss of capacity to activate protein C and increased amount of bound thrombin activity in rabbit vein grafts explanted between 3 and 42 days after implantation. Data is mean±SEM of n=3 grafts per time point.

EXAMPLE 4

Local In Vivo Thrombin Inhibition by Viral Vector-Mediated Gene Transfer of TM The above example demonstrates the association between loss of TM expression and enhanced local thrombin activation. Strategies that prevent TM loss or restore TM expression would be expected to restore the capacity of the graft to generate APC and to reduce or abolish local thrombin activation. If effective, such strategies could significantly reduce the rate of early vein graft failure. The present example uses a first generation adenovirus vector to restore TM expression by rabbit vein grafts.

A. Optimization of Adenovirus—Mediated Gene Transfer to Rabbit Vein Grafts

Experiments were performed to determine the optimal dose of adenovirus vector to achieve effective gene transfer to vein grafts. Rabbit vein grafts were transduced as described in Example #1 with ascending doses of AdCNLacZ, a first-generation adenovirus vector expressing the marker gene, nuclear-targeted β-galactosidase. On day 3, grafts were harvested and ∃-galactosidase antigen was determined in vessel extracts using ELISA and normalized to total protein (FIG. 6A). Results are the mean of n=4±SEM vessels per dose. ∃-galactosidase expression reached a plateau at a dose of $3.75 \times 10^{10}$ plaque forming units (pfu)/ml. This was the dose used for all subsequent studies. To determine the duration of transgene expression, grafts were harvested at the indicated times and the vessel extracts assayed for β-galactosidase expression by ELISA (FIG. 6B). Results are the mean of n=4±SEM per time-point. Transgene expression peaked on day 6 and fell off rapidly by day 9. No β-galactosidase antigen was detected in untransduced vessels. FIG. 6C shows a macroscopic view of the lumenal surface of a rabbit vein graft transduced with AdCNLacZ at a dose of $3.75 \times 10^{10}$ pfu/ml and harvested on day 3. The blue color denotes successful gene transfer and β-galactosidase expression. The arrows indicate the arteriovenous anastomoses.

Figure 7A:
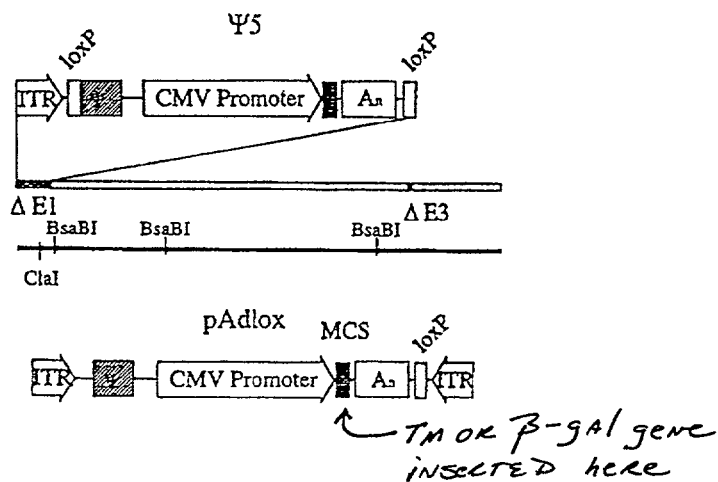
FIGS. 7A-B are schematic drawings showing construction of thrombomodulin (TM) and β-galactosidase encoding adenovirus vectors.
Figure 7B:
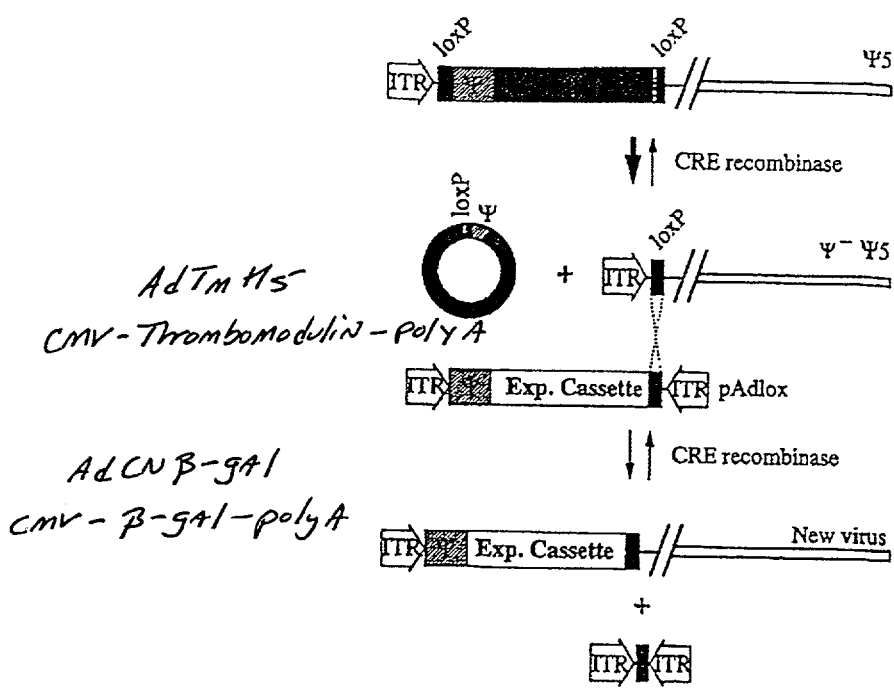

FIGS. 7A-B are schematic drawings showing construction of ADCNLacZ and ADTmh5. See Hardy, S. et al. (1997), supra, for a description of the abbreviations.

B. Adenovirus—Mediated Transfer of Thrombomodulin to Rabbit Vein Grafts

Figures 8A, 8B:
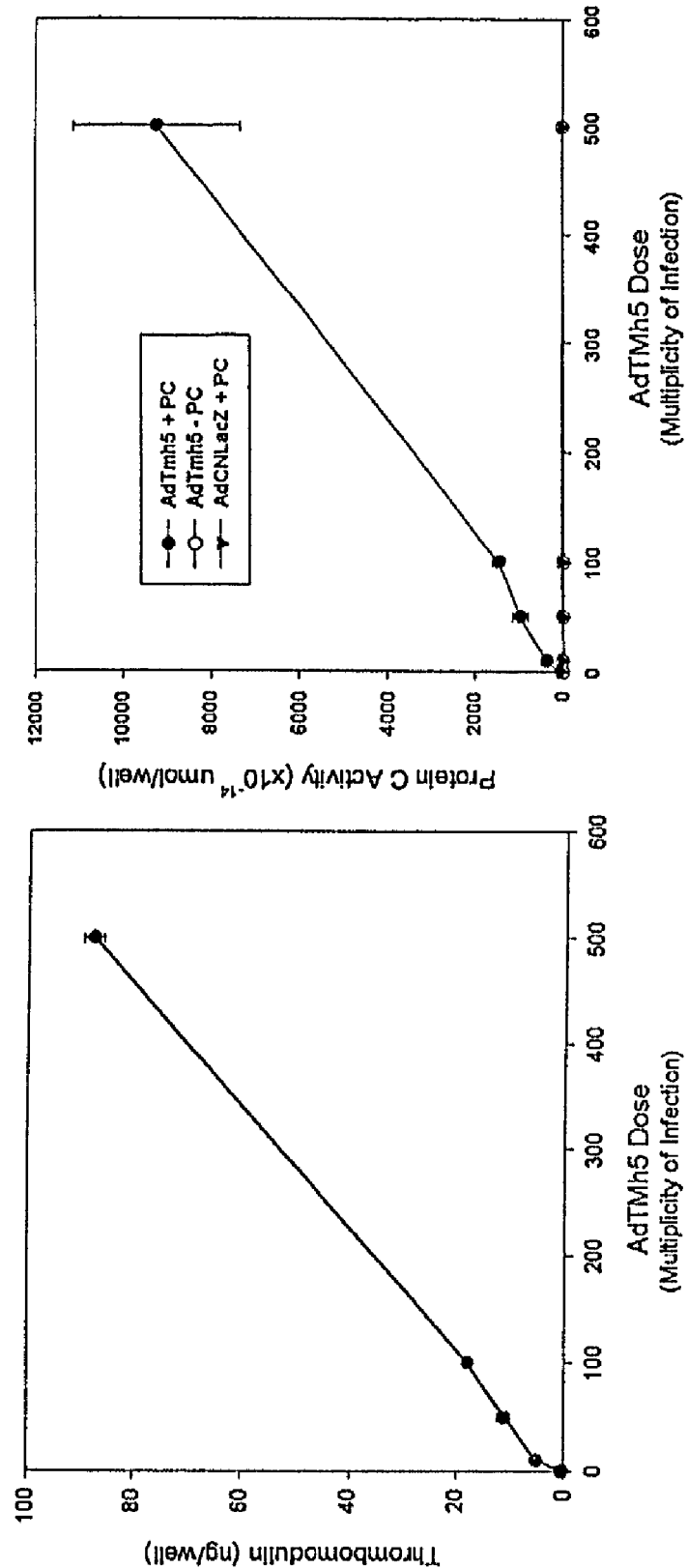
FIGS. 8A-B are graphs showing dose-dependent adenovirus-mediated thrombomodulin expression as determined by ELISA specific for human thrombomodulin (FIG. 8A) and Protein C assay (FIG. 8B). AdTmh5 is an adenovirus vector encoding human TM. AdCNLacZ is the same adenovirus vector except that it encodes β-galactosidase.

The cDNA encoding human TM gene was obtained from the American Type Culture Collection (ATCC) cloned into a shuttle vector and a first-generation adenovirus vector (AdTMh5) was generated by standard methods as depicted in FIG. 7. Transduction of rabbit jugular venous endothelial cells results in a dose-dependent increase in the expression of TM antigen and in the capacity to activate protein C (FIGS. 8A and 8B). TM expression was quantitated by antigen (FIG. 8A) using an ELISA specific for human TM and activity (FIG. 8B) using a protein C assay as described above. Values are the mean of n=3±SEM.

Figure 9:
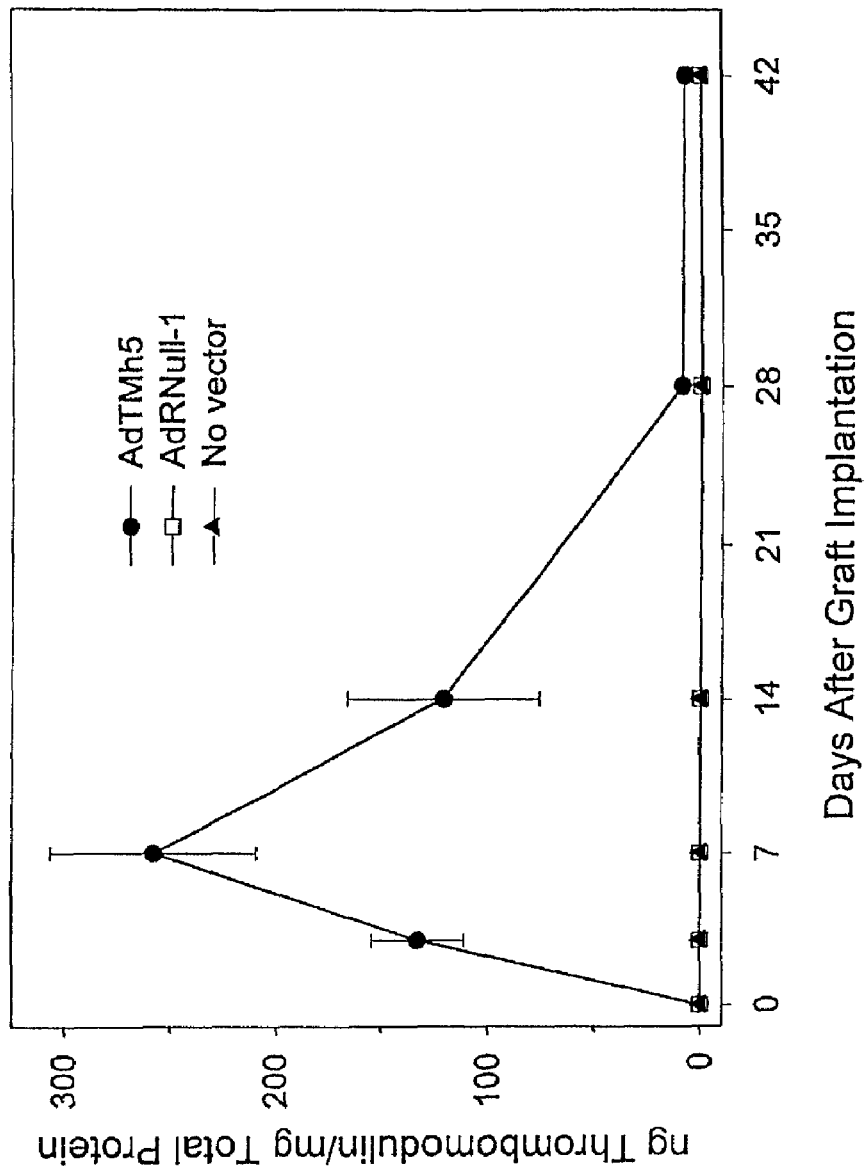
FIG. 9 is a graph showing duration of thrombomodulin (TM) expression in rabbit jugular venous endothelial cells.

Following these in vitro experiments, the ability of AdTMh5 to mediate in vivo expression of human TM by transduced rabbit vein grafts was evalated. Rabbit vein grafts were transduced with either no virus, $3.75 \times 10^{10}$ pfu/ml of AdTMh5 or AdNull-1, an identical adenovirus vector expressing no transgene. Transduction of rabbit vein grafts with of AdTMh5 resulted in significant expression of the human TM protein by graft endothelial and smooth muscle cells on day 3 as assessed by immunohistochemical detection with a human TM-specific monoclonal antibody (American Diagnostica). TM expression was quantified in vessel extracts using an ELISA specific for human TM and normalized to total protein (FIG. 9). Adenovirus-mediated human TM expression peaked on day 7 and remained substantial for over 14 days. Surprisingly, TM expression was detectable, albeit in small amounts, for up to 42 days. Untransduced and AdNull-1-transduced grafts did not have any detectable amounts of human TM an any time point.

FIG. 9 demonstrates the magnitude and duration of adenovirus-mediated expression of human TM by transduced rabbit vein grafts. Values are mean of n=3 animals±SEM.

EXAMPLE 5

Restoration of Thrombomodulin Expression Increases APC Generation and Decreases Thrombin Activation Examples #2 and #3 illustrate the concept that loss of TM expression reduces the capacity of vein grafts to generate APC and the consequent enhancement of local thrombin activation that causes early graft failure. Example #4 illustrates how adenovirus-mediated gene transfer can effectively restore TM expression by transduced vein grafts. We sought to determine whether adenovirus-mediated TM expression would then result in retoration of APC-generating capacity and reduced local thrombin generation.

Figure 10:
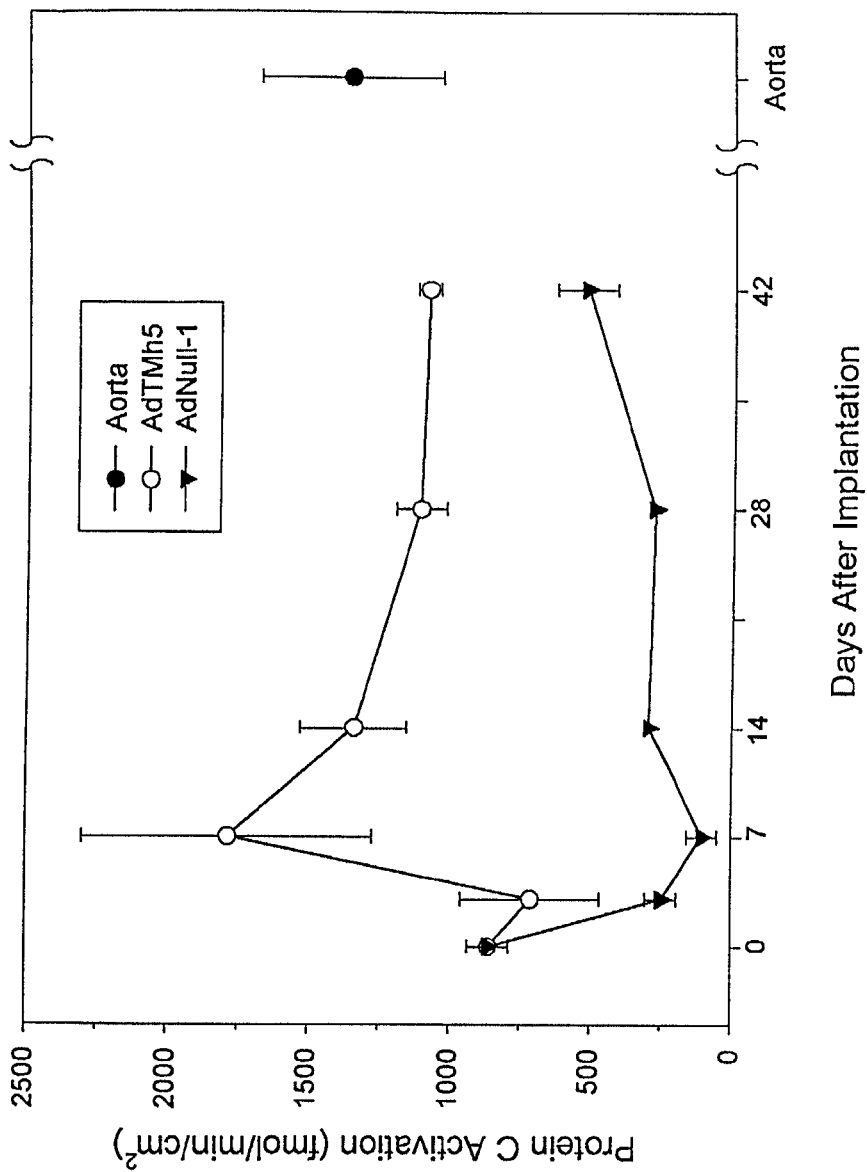
FIG. 10 is a graph showing in situ protein C activation in AdTmh5 transduced rabbit vein grafts harvested at the indicated times.

Rabbit vein grafts were transduced with $3.75 \times 10^{10}$ pfu/ml of either AdTMh5 or AdNull-1 and the capacity to generate APC was measured between 1 and 42 days after implantation (FIG. 10). Transduction with AdTMh5 resulted in a supraphysiologic restoration of the graft's ability to generate APC. This effect peaked on day 7 but was present as late as 42 days after implantation.

FIG. 10 is described in more detail. In situ protein C activation in transduced rabbit vein grafts harvested at the indicated times. Data is mean±SEM of n=3 grafts per time point. Day=0 are untransduced jugular veins. Values for normal aorta segments are shown for comparison.

Figure 11:
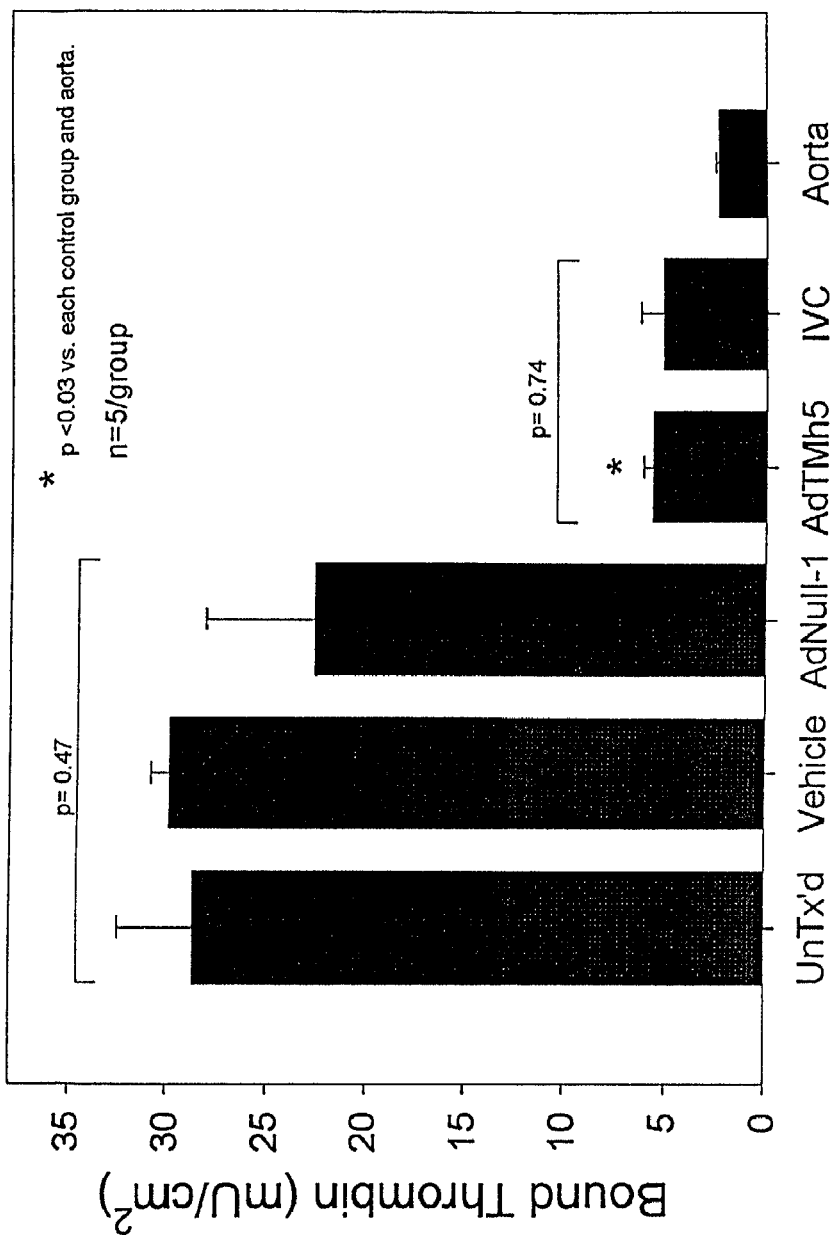
FIG. 11 is a bar graph illustrating human TM expression following adenovirus-mediated gene transfer of rabbit vein grafts as a function of implantation time. Untx'd=untransduced. IVC=normal rabbit inferior vena cava.

Bound thrombin activity was measured on day 7, the time of peak activation, in grafts transduced in similar fashion with no virus, vehicle control, AdTMH5 or AdNull-1 (FIG. 11). Transduction with AdTMh5 reduced the amount of bound thrombin activity by approximately 85% compared to controls, to a level similar to that found on normal rabbit veins. This confirms the hypothesis that restoration of TM expression likewise restores the capacity of vein grafts to generate APC thus inhibiting local thrombin activation.

FIG. 11 is explained in more detail as follows. Transduced and control rabbit vein grafts were harvested on day 7 and bound thrombin activity measures in situ. Values are the mean±SEM of n=5 grafts per group. Values for normal rabbit inferior vena cava (IVC) and aorta are shown for comparison. Untx'd=untransduced grafts. Vehicle=grafts incubated with vehicle without virus.

EXAMPLE 6

Alterations in Thrombomodulin Expression in Human SVG

It is possible to detect and quantitate expression of human thrombomodulin in fixed sections of human saphenous vein graft (SVG). Preferred specimens are from patients who expired at various times after coronary artery bypass surgery (range hours to years). Specimens can be either formalin-fixed and paraffin-embedded or prepared in OCT for cryo-sectioning. An objective is to compare the alterations in the expression of TM in human SVG that was observed in rabbit vein grafts. Correlations between loss of TM and expression and the timing of vein graft failure can then be made.

The following protocol can be used. Tissue sections are stained for human TM using a mouse monoclonal anti-human TM antibody, DakoTM 1009 (Dako, Calenteria, Calif.). This antibody recognize TM in fresh-frozen or paraffin-embedded sections. Sections are incubated with the appropriate biotinylated secondary antibodies and incubated with horseradish peroxidase-labeled streptavidin. Peroxidase activity (red reaction product) is revealed by amionethylcarbazole (Dako). Cellular components (ie., SMCs, endothelium, and macrophages) are identified using cell specific antibodies. Both TM and TF expression is quantitated as previously described using a computerized imaging system consisting of a DMC digital microscopic camera (Polaroid, Cambridge, Mass.) mounted on an Olympus BX 60 microscope (Olympus America, Melville, N.Y.) linked to a PC computer using SigmaScan 4.0 software (SPSS, Chicago, Ill.). Specifically, sections stained with the appropriate antibody and counter stained with hematoxylin are digitized and the area of interest (i.e. intima, neointima or media) highlighted using a cursor with exclusion of background staining. The degree of color intensity in the selected areas is quantitated using color threshold analysis. An average of the four vessel quadrants is calculated for each section and the mean of four vessel sections, each at least 75:m apart, can be determined. In this way, it is possible to quantitate neointima and medial thrombomodulin and tissue factor expression.

The early expression pattern of TM and the subsequent effects on the ability to activate protein C can be examined over time by human SVG placed in organ culture. Surplus SVG segments are obtained at the time of coronary artery or peripheral bypass surgery and placed into organ culture. SVG segments placed in organ culture remain viable for at least 14 days and retain their endothelial cell integrity. This model has been used to investigate the pathobiology of vein graft neointimal hyperplasia as well as to perform gene transfer experiments. Measurement of TM protein expression and the graft's ability to activate protein C will be measure as described above.

More specifically, SVG segments are obtained from patients undergoing coronary artery bypass surgery. The "surgical preparation" of these surplus segments is identical to that of the implanted segments and includes, adventitial stripping, side-branch ligation, gentle manual distension and storage in heparinized saline for 30-120 minutes. The segments are collected in pre-warmed RPMI media buffered with 20 nM HEPES and containing 2 mM glutamine, 0.225 mg/ml papaverine hydrochloride (Sigma, St. Louis, Mo.) and 1× antibiotic/antimycotic solution (Biofluids, Rockville, Md.). The segments are opened longitudinally then cut transversely in 5-10 mm lengths and cultured with the lumenal side up in HEPES-buffered RPMI media containing 2 mM glutamine, 1× antibiotic/antimycotic solution and 30% heat inactivated fetal calf serum (Sigma) at 37° C. and under 5% $CO_2$.

EXAMPLE 7

Long-Term Expression of Thrombomodulin to Human SVG Using Adeno-Associated Virus-mediated Gene Transfer It has been found that adenovirus-mediated delivery of bioactive proteins to the vessel wall is relatively efficient. However, given the transient nature of transgene expression, proinflammatory response and vector immunogenicity in some settings, it will be helpful to maximize clinical applicability to promote long-term genetic modification of human vein grafts. Adeno-associated virus (AAV) is a non-pathogenic human parvovirus that requires a helper virus (adenovirus or herpes virus) for replication. Several features make recombinant AAV an attractive vector for gene transfer: 1) AAV stably integrates into the target cell genome facilitating sustained transgene expression, 2) like adenoviruses, AAV vectors can transduce non-dividing cells, 3) AAV particles can be purified to high titers, 4) integration of the AAV provirus produces no apparent untoward effects on target cell phenotype, 5) AAV vectors have a broad tissue tropism and 6) AAV vectors do not appear to engender a host immune response. For these reasons, AAV vectors are currently being used in several human gene therapy clinical trials.

AAV vectors have been used for in vivo vascular gene transfer. For example, Gnatenko et al. reported that intraluminal delivery of a recombinant AAV vector expressing ∃-galactosidase resulted in infection of nearly 100% of cells throughout the intima and media of un-injured rat carotid arteries. Infection was assessed using in situ PCR and may not reflect the ability of the virus to express the transgene. Quantitative β-galactosidase expression was increased 20-fold compared to controls. This magnitude of expression is similar to what was found with adenoviral vector-mediated expression of β-galactosidase in injured rat carotid arteries, where typically 30% of medial SMC are transduced. Rolling et al. found that both injured and uninjured rat carotid arteries transduced with a similar AAV virus expressed β-galactosidase for at least 20-30 days. Because of the potential for long-term transgene expression, AAV vectors appear to be adaptable for genetic modification of human autologous SVG. Use of particular AAV vectors are discussed in Section A, below.

The AAV vectors of this example can be used to facilitate large scale viral preparation and infection of human SVG. In particular, it is possible to determine ability of AAV vectors to infect human SVG in organ culture and determine the kinetics of transgene expression. These experiments can be used as a compliment of those being performed using the rabbit vein graft model. Also, it will be possible to seek to develop and optimize a transduction protocol that could be used in a human clinical trial.

A. Vector Construction

A recombinant AAV vector, AAV$_2$hTM, expressing human thrombomodulin (TM) can be generated as previously described for AAV$_2$β-gal, a control vector expressing β-galactosidase (see Zabner et al. (2000) *J Virol* 74:3852 and Chiorini et al. (1995) *Hum Gene Ther* 12:1531 for details of recombinant vector generation). The TM cDNA is cloned into the shuttle vector pAAVRnLacZ after excision of the nLacZ cDNA. This shuttle vector contains two flanking AAV inverted terminal repeat (ITR) sequences, the Rous sarcoma virus long terminal repeat promoter and a downstream simian virus-40 polyadenylation signal. AAV ITR sequences are required cis-acting elements necessary for viral replication. The shuttle vector and a helper plasmid, pSV40oriAAV, are co-transfection into COS cells using electroporation. pSV40OriAAV contains the AAV Rep and Cap genes, encoding for the requisite replication and structural proteins, respectively. Following co-transfection, COS cells are infected with wild-type adenovirus and harvested 72 hours later. Crude viral lysates are heated to inactivate the helper adenovirus then purified by cesium chloride centrifugation. Purified viral stocks will be titered by the dot-blot hybridization method and tested for wild-type AAV and helper virus contamination. This method has produced viral stocks with titers of up to $10^{11}$ infectious units (IU)/ml.

B. Gene Transfer into Saphenous Vein Grafts (SVG)

Surgically prepared SVG graft segments will be washed extensively to remove and residual heparin, then divided and cannulated as described in Example 1, above. Heparin has been shown to inhibit AAV type 2 transduction by competing for viral cellular receptors. Segments (n=10 in each group) will be transduced with AAV, β-galactosidase in doses ranging between $10^9$-$10^{11}$ IU/ml as described above. Because human umbilical vein endothelial cells infected with a recombinant AAV vector expressing β-galactosidase do not manifest significant transgene expression for 5 to 7 days SVG segments will be assayed for β-galactosidase expression by ELISA on day 7. Once an optimal dose is determined, segments (n=10 in each group) will be transduced and harvested at various times over the 14 day period (and beyond if the graft survives) to determine the kinetics of transgene expression. Experiments will also be performed to determine the optimal dwell time and vehicle.

Because AAV vectors are significantly smaller than adenoviral vectors (20 nm vs. 100 nm, respectively), the tissue distribution following lumenal delivery is likely different than for adenovirus vectors. It has been reported in several species that the intact endothelium is an impregnable barrier to transduction of medial smooth muscle cells following intralumenal delivery of an adenoviral vector. This is in contrast to what was reported both by Rolling and Gnatenko who demonstrated significant medial cell transduction by AAV vectors in uninjured arteries. Because the endothelium of vein grafts is partially denuded during implantation it is believed that significant medial SMC-transduction is a result. It is possible to quantitate the transduction efficiency of medial smooth muscle and adventitial cells compared to endothelial cells using digital imaging analysis.

Following pilot experiments using AAV$_2$β-gal, TM expression is optimized in SVG segments transduced with AAV$_2$hTM. It is possible to compare the extent and duration of AAV versus adenovirus mediated TM expression. The effect of AAV$_2$hTM-mediated TM expression on thromboresistance and atherosclerosis can be assessed as described above in Examples #3 and #4.

EXAMPLE 8

Expression of EPCR in Rabbit Vein Grafts

The expression of TM by endothelial cells is one of the key determinants of vascular thromboresistance. A 235 amino acid endothelial cell-specific trans-membrane protein that binds protein C has recently been discovered and named endothelial cell protein C receptor (EPCR). EPCR binds protein C (Kd=30 nM) and "presents" it to the thrombin/TM complex, thus augmenting the rate of protein C activation. EPCR is expressed predominantly by the endothelium of large arteries and veins. The in vivo regulation of EPCR activity is not as well defined as it is for TM. Like TM, the EPCR gene is down-regulated by exposure to inflammatory cytokines such as TNF-α. It is unknown what effect shear stress has on EPCR expression.

Human umbilical vein endothelial cells in culture express ~700,000 molecules of EPCR/cell, compared with ~100,000 molecules of TM/cell. Inhibiting protein C binding to EPCR with a blocking antibody reduces protein C activation by over 9-fold. Furthermore, reconstitution studies performed in phospholipid vesicles indicate that at constant TM concentrations, protein C activation is proportional to the EPCR concentration and does not saturate at an EPCR:TM ratios as high as 14:1. These data suggest that; 1) in order to understand pathologic alterations protein C activation one must understand alterations in both TM and EPCR expression, and 2) strategies aimed at maximizing in vivo protein C activation might potentially include augmentation of both TM and EPCR expression.

The polyclonal goat antibodies gt 262αmEPCR and gt αpgtEPCR have been obtained. These antibodies are directed against mouse and human EPCR. Also provided us was the cDNA encoding human EPCR (see Fukudome and Esmon (1994) *J Biol Chem* 269:26486). Studies demonstrating that both of these antibodies will recognize rabbit EPCR in OCT-frozen tissue have been conducted. It is possible to optimize the staining parameters, characterize the specificity of each antibody and to determine whether the EPCR epitope is recognized in formalin-fixed tissue as is TM using standard procedures.

EPCR protein expression will be determined in rabbit vein grafts harvested between 1 and 42 days (n=4 vessels per time point) after implantation, in analogous fashion to TM. Unmanipulated contralateral jugular veins (day=0 timepoint) and carotid arteries will serve as controls. OCT-frozen sections (or perfusion formalin-fixed sections if possible) will be sectioned such that we obtain four 5 μm-thick slices, at least 75 μm apart. The tissue will be stained with the anti-EPCR antibody and incubated with an appropriate biotinylated secondary antibody followed by horseradish peroxidase-labeled streptavidin. Peroxidase activity (red reaction product) will be revealed by aminoethylcarbazole (Dako). EPCR protein expression will be quantitated using a computerized imaging system consisting of a DMC digital microscopic camera (Polaroid, Cambridge, Mass.) mounted on an Olympus BX 60 microscope (Olympus America, Melville, N.Y.) linked to a PC computer using SigmaScan 4.0 software (SPSS, Chicago, Ill.). The intima layer will be masked and the degree of color intensity in the red spectrum will be quantitated using color threshold analysis. The number of pixels reaching threshold will be expressed as arbitrary units (AU) and normalized to millimeter of luminal perimeter. To insure that decreased EPCR expression is not due to endothelial cell loss, adjacent sections will be stained in similar fashion with the mouse monoclonal anti-vWF antibody, F8/F6 (Dako) and analyzed in similar fashion.

EXAMPLE 9

Construction of Adenovirus Vectors Expressing TM and EPCR

We will determine whether co-expression of TM and EPCR can maximize protein C activation more than expression of TM alone. To accomplish this, we will first construct an expression cassette consisting of an RSV promoter, SV-40 polyadenylation signal and full-length human EPCR cDNA fused at the 3' terminus to the sequence encoding for the FLAG epitope (D-Y-K-D-D-D-D-K) SEQ ID NO: 1. Tagging of the EPCR protein with the FLAG epitope does not alter its activity and will permit easier recognition and quantitation of the expressed EPCR protein by indirect ELISA (utilizing a biotinylated M-2 monoclonal antibody; Sigma). An adenovirus vector, AdEPCR-F, will be generated that expresses the tagged human EPCR protein.

COS cells, which do not express TM (as previously determined by western blot analysis and in situ protein C activation assay) will be co-transduced with varied doses of AdTMh5 and AdEPCR-F such that the total dose of virus remains constant at a multiplicity of infection (MOI) of 100 virions/cell. TM and EPCR protein expression will be determined on day 3 by ELISA and protein C activation will be determined by modification of the in situ assay described above for use on cells in culture. In this way, we will determine what relative ratio of TM to EPCR protein expression results in maximal protein C activation for a given total dose of virus. Comparisons will be made to the level of protein C activation produced by transduction with either virus alone at an MOI of 100.

A limited series of vectors will be generated to test the concept that protein C activation can be optimized by expressing both TM and EPCR in the same vector under the control of a strong promoter. We will employ use of a polio virus internal ribosome entry site (IRES) element to direct transcription from a single promoter of a bicistronic mRNA that encodes for both proteins. This will permit high-level translation of both proteins while avoiding promoter interference that may occur if two separate promoters are used. The relative positioning of the TM and EPCR genes to the IRES element will be determined from the results of the above experiment, as genes located 5' to the IRES are translated slightly more efficiently that genes located 3' (2:1 to 3:2 ratio). All expression cassettes are within the packaging size limit for the vector. The promoters to be tested include; 1) the Rous sarcoma virus LTR promoter (RSV) used in AdTMh5, 2) the mouse CMV immediate early promoter (mCMV), which has been shown to be 5-30-fold stronger than the traditional human CMV immediate early promoter, 3) the mouse U1small nuclear RNA promoter,[24] and 4) the human ICAM-2 promoter which has been shown to drive high-level endothelial cell-specific transcription of heterologous genes.

To determine the effect of combined TM and EPCR expression on restoration of protein C activation in vivo, rabbit vein grafts (n=8 per group) will be transduced with either no virus, AdRNull-1 or the optimized vector expressing TM and EPCR. On day 7 the graft will be harvested and the capacity to generate APC will be determine using the in situ assay described in Example #3.

EXAMPLE 10

Time-Course of Vein Graft Inflammation

There is recognition that vein grafts develop inflammatory infiltrates after implantation. However, the temporal expression of specific inflammatory mediators has not been thoroughly characterized. Because exposure to cytokines is known to down-regulate TM and EPCR gene expression, it would be important to correlate the time course of endothelial cell activation and inflammation with TM and EPCR expression. This data would also provide support for the prevention of graft failure using strategies that limit these changes.

The OCT-frozen sections of grafts and control vessels harvested in Example 8 can be stained for several markers of inflammation and subjected to digital immunohistochemical analysis. The well-characterized monoclonal antibodies Rb 1/9 and Rb2/3 which recognize rabbit VCAM-1 and ICAM-1, respectively were obtained from Dr. Myron Cybulski (University of Toronto). Commercially available antibodies that detect rabbit epitopes that will be used include: BBA32, a polyclonal Ab recognizing rabbit P-selectin (R&D Systems); RAM11,a monoclonal Ab recognizing macrophages (Dako); CBL 486, a monoclonal Ab recognizing CD-40 (Cymbus Biotechnology); M158, a monoclonal Ab recognizing CD40 ligand (Immunex); KEN-5, a monoclonal Ab recognizing T lymphocytes (Serotec); K50891R, a polyclonal Ab recognizing neutrophil peroxidase (Biodesign); and 2C4, a monoclonal Ab recognizing Class II MHC (BD Pharmingen). Histologic sections are counterstained with hematoxylin, incubated with appropriate primary and biotinylated secondary antibodies followed by horseradish peroxidase-labeled streptavidin then developed with aminoethylcarbazole.

Quantitation of endothelial cell ICAM-I, VCAM-1I, P-selectin Class II MHC, and CD-40 staining is performed using digital immunohistochemical analysis as described above for TM and EPCR protein expression. The number of adherent or infiltrating neutrophils, macrophages, T lymphocytes and CD-40L-positive cells (platelets and lymphocytes) will be determined for each section using combined spectrum-specific intensity and size threshold analysis and summed to determine a mean for each vessel. Difference between the means of all vessels of a given time point will be compared using one-way ANOVA.

EXAMPLE 11

Effect of Adenovirus-Mediated Transfer of both TM and EPCR on Vein Graft Thrombosis and Inflammation An invention objective is to determine whether restoring thromboresistance can prevent graft failure. It is possible to determine the effects of viral-mediated enhancement of protein C activation on early graft thrombosis. Because there is evidence that protein C has potent anti-inflammatory effects and that inflammation plays a causal role in graft failure, it is also possible to investigate the effects on endothelial cell activation and the expression of several mediators of the inflammatory response.

In the standard rabbit vein graft model, despite the fact that significant platelet and fibrin deposition was not seen on the lumenal surface by scanning electron microscopy, complete thrombotic occlusion of the grafts occurs in less than 5% of animals. Therefore, it is feasible to modify the model in order to introduce an additional thrombotic stimulus that will allow a determination of whether enhanced protein C activation can prevent early graft occlusion.

Accordingly, rabbit vein grafts can be surgically exposed and a snare ligature will be placed around the carotid artery, proximal to the graft anastomosis. A perivascular doppler flow probe connected to a Transonic T106 flowmeter will be used to measure changes in graft blood flow velocity induced by snare constriction. In a pilot group of n=5 rabbits we will determine what degree of constriction, as measured by a decrease in average peak graft blood flow velocity, will result in significant cyclic flow variations (CFV) within a 60 minute period that are indicative of active platelet and thrombus deposition. See Willerson J. T. et al. (1991) *PNAS (USA)* 88: 10624. A significant CFV will be defined as >50% reduction in average peak flow velocity after application of the ligature.

To determine the effect of augmented protein C activation, rabbit vein grafts (n=8 per group) can be transduced with either no virus, AdRNull-1 or the optimized vector expressing TM/EPCR. On day 7 the animals are anesthetized and the grafts exposed. Following the predetermined restriction of blood flow with the snare, the number of significant CFV within 1 hour is determined. The group averages will be compared using one-way ANOVA. At the end of the measurement period, animals are administered 1000 U of intravenous heparin sulfate (to prevent post-mortem thrombosis) and the grafts immediately perfusion fixed with 10% formalin and removed. Grafts are sectioned into 4 slices as described above and stained with phosphotungsten acid hematoxylin which detects fibrin. The percent lumenal occlusion by thrombus is determined for each graft using digital image analyasis. The average percent of lumenal occlusion for each group is compared using one-way ANOVA Given that protein C may have anti-inflammatory properties, it is possible to determine the effects of over-expression of TM/EPCR on endothelial cell activation and graft inflammation. Vein grafts (n=5 group) transduced with either no virus, AdRNull-1 or the optimized vector expressing TM/EPCR are harvested at a time when inflammatory changes and endothelial cell activation are maximal (determined above). OCT-frozen sections will be stained and digital images analyzed for the expression of ICAM-1, VCAM-I,CD40 and class II MHC and the presence of macrophages, neutrophils, T-cells and CD40L positive cells using the antibodies and methods described in Example 10. The average values for each group are compared using one-way ANOVA.

EXAMPLE 12

Augmentation of TM Expression via Manipulation of TM Regulatory Pathways

Transfer of the TM gene is one method to restore TM protein expression and thromboresistance to vein grafts. It is possible that manipulation of the expression and/or activity of molecules in the TM regulatory pathway may also lead to restoration of TM protein expression. It is known for example that TNF-α stimulation of endothelial cells results in a profound down-regulation of TM gene expression. Given the profound inflammatory response in vein grafts (see FIG. 2) it is reasonable to believe that TNF-α elaboration by activate monocytes or lymphocytes might play a role in loss of TM expression in vein grafts. The mechanism by which TNF-α mediated TM regulation is unknown but it is believed that activation of the transcription factor, nuclear factor-κB (NF-κB), may play a prominent role.

The transcription factor nuclear factor-6B (NF-6B) is an important regulator of the expression of many genes that mediate immune and inflammatory responses. It is expressed in a number of cell types, including vascular endothelial cells, pulmonary epithelial cells and macrophages. NF-6B is a heterodimer composed mostly of two subunits, p65 (also called relA) and p50. In unstimulated cells it exists in the cytoplasm complexed to a family of inhibitory proteins called I6B. I6B masks the nuclear localization signal present on NF-6B, thereby preventing it from being translocated into the nucleus. Following cellular activation by a wide variety of stimuli, I6B∀ is phosphorylated by specific kinases, causing its dissociation from NF-6B and marking it for degradation by proteosomes. Following its release, NF-6B is translocated to the nucleus where it binds to specific sequences in the promoter region of target genes, enhancing their transcription.

We have obtained the cDNA encoding a FLAG epitope-tagged dominant-negative I6Bα mutant (I6Bα-S32A/S36A). See Brockman et al. (1995) *Mol Cell Biol* 15:2809. Mutation of serine residues 32 and 36 prevents I6Bα from being phosphorylated and degraded. Constitutively active I6Bα remains bound to NF-6B in the cytoplasm, thus preventing its translocation into the nucleus in response to inflammatory stimuli. Several groups have demonstrated that over-expression of similar dominant-negative I6Bα mutants can prevent in vitro endothelial cell NF-6B activation and expression of inflammatory molecules by TNF-∀. We have successfully generated a first generation adenovirus vector, AdIκBS32/36A, that expresses this mutated form of I6Bα. Preliminary experiments in our laboratory have confirmed that transduction of endothelial cells with AdIκBS32/36A prevents NF-6B activation in response to TNF-α.

Figure 12:
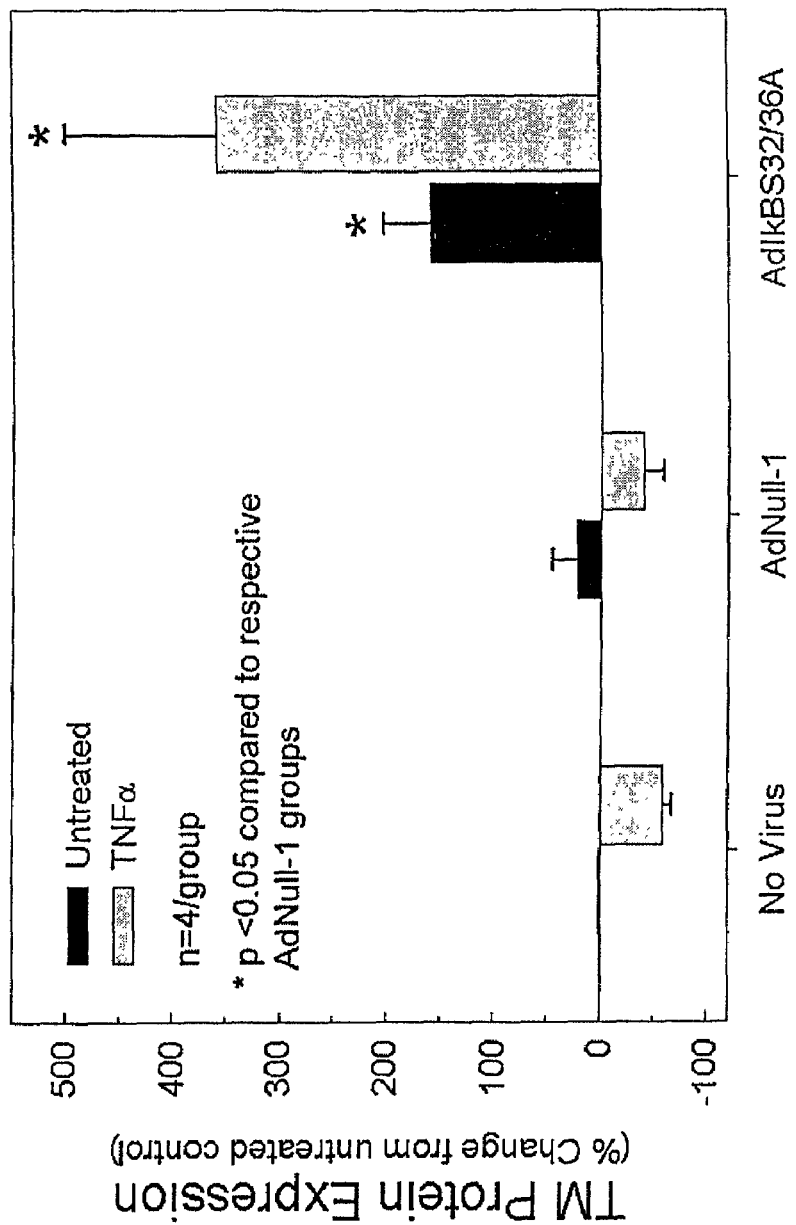
FIG. 12 is a bar graph showing effects of NF-κB inhibition on thrombomodulin (TM) expression. AdIκBS32/36A=adenovirus vector encoding a mutated form of factor 16Bα.

To assess the effects of NF-κB inhibition on thrombomodulin expression, human umbilical vein endothelial cells (HUVEC) in culture were transduced with either no virus, AdNull-1 or AdIκBS32/36A at a multiplicity of infection of 50 pfu/cell. Two days after infection, cells were either left unstimulated or treated with 5.7 nM human TNFA (Clontech, Palo Alto, Calif.) for 18 hours. TM protein expression was then assessed in cell extracts by quantitative Western blot analysis (FIG. 12). Not only did NF-6B inhibition prevent TM down-regulation in response to TNF-∀ stimulation but it unexpectedly resulted in apparent up-regulation of TM protein expression in both unstimulated and TNF-α stimulated cells.

The involvement of NF-□B activation in the down-regulation regulation of TM expression provides a rationale for the use of the NF-κB inhibitors to prevent early vein graft failure. We are performing experiments investigating the effects AdIκBS32/36A transduction on rabbit vein graft inflammation, TM expression, protein C activation and local thrombin activation.

EXAMPLE 13

Effects of Restoration of TM Expression on the Development of Atherosclerosis

In addition to its potent anticoagulant effects, APC has been shown to have anti-inflammatory properties (reviewed in Esmon et al. (1991) *Thromb Haemost* 66:160 and Esmon (1998) *Immunologist* 6:84). Loss of TM expression and subsequent loss of local APC generation likely contributes to the inflammatory response seen in vein grafts following implantation. Inflammation is also a major component of the development of atherosclerosis (reviewed in Ross (1999) *Am Heart J* 138:S419 and Libby (2000) *Am J Cardiol* 86:3J). We hypothesize that reducing vein graft inflammation will prevent the development of atherosclerosis, the major cause of late vein graft failure.

The rabbit vein graft model detailed in Example #1 is has also be adapted to study the effects hypercholesterolemia on the development of graft atherosclerosis (Zwolak et al. (1989) *Arterioscler* 9:374). Rabbits fed atherogenic diets consisting of 0.2% cholesterol for one month prior to graft implantation develop exuberant neointimal thickening with marked infiltration of foam cells (lipid-laden macrophages) 2 to 6 months after surgery. We will determine the effects of restoration of TM expression on inflammation and the development of atherosclerosis.

Rabbits (n=10/group) will be fed an atherogenic diet (1% cholesterol) beginning 1 week prior to surgery. Vein graft segments will be transduced with no virus, AdTH5 or AdNull-1 at a dose of $3.75 \times 10^{10}$ pfu/ml. One group of animals will be sacrificed on day 7 and the degree of acute inflammation will be assessed using immunohistochemical staining for inflammatory markers described in Example #10. Another group of animals will be sacrificed at 12 weeks, the grafts segments harvested and divided. One segment half will be formalin-fixed for vessel morphometric analysis, the other half will be freeze-sectioned and stained with RAM-11, a monoclonal antibody recognizing rabbit macrophages in tissue but not circulating or adherent monocytes (Dako). The degree of foam cell accumulation (a marker of atherosclerosis) will be quantitated using a visual scoring system and related to neointimal mass. Serum will be obtained at the time of surgery and at sacrifice to document elevated lipid levels. We anticipate that restoration of TM expression will decrease vein graft inflammation and will prevent the development of atherosclerosis.

EXAMPLE 14

Augmenting TM Expression by Seeded Prosthetic Grafts

Synthetic vascular grafts, constructed out of Dacron, Teflon or Gore-Tex, are frequently employed by surgeons performing large vessel, infrainguinal revascularization procedures. More widespread use of prosthetic grafts for coronary and small-vessel peripheral arterial bypass procedures is precluded by the extremely high rates of failure in grafts with diameters<4 mm due to early thrombosis (See Clowes, A. W. (1993) *Cardiovasc Pathol* 2:179S). Seeding of grafts with autologous endothelial cells is one method to reduce the thrombogenicity of prosthetic grafts that has been shown to marginally improve graft patency in vivo (reviewed in L. Bordenave et al. (1999) *Endothelium* 6:267 and P. Zilla (1991) *Curr Opin Cardiol* 6:877).

Genetic modification of seeded endothelial cells to resist thrombosis has been advocated to further improve the performance of small-diameter prosthetic grafts (reviewed in G. Vassalli et al (1997) *Cardiovasc Res* 35:459. Retrovirus vectors, and potentially adeno-associated virus vectors, are ideally suited for ex vivo transduction of endothelial cells that will permit long term expression of anticoagulant molecules.

Exposure of endothelial cells in culture to increased shear stress has been shown to cause down-regulation of TM gene expression (A. M. Malek et al. (1994) *Circ Res* 74:852). We hypothesize that expansion of autologous endothelial cells in vitro will result in impaired in vivo TM expression and APC-generating capacity when these cells are used to seed prosthetic vascular grafts. Furthermore, we posit that genetic modification of endothelial cells with retrovirus vectors expressing human TM will improve the thromboresistance and patency of small-diameter prosthetic grafts after implantation.

We will test this first hypotheses by determining the change in TM expression when endothelial cells are expanded in culture, seeded onto a prosthetic graft and subjected to arterial shear stress using an ex vivo perfusion system. If TM expression is found to be impaired in seeded endothelial cells, we will determine the effect of ex vivo transduction of these cells with a retrovirus expressing human TM.

Our laboratory has recently acquired an ex vivo perfusion system consisting of a high-flow pump and a perfusion chamber able to accommodate a variety of vascular conduits. The system fits into an incubator warmed to 37° C. with 5% $CO_2$. Preliminary experiments indicate that the pump can deliver flow rates of up to 125 ml/min which, in 2 mm diameter prosthetic graft can generate up to 25-50 dyne/$cm^2$ of shear stress on the graft luminal surface. We have established characterized primary cultures of endothelial cells harvested from a rabbit jugular vein and aorta. Cells are grown in EGM media (Clonetics) under standard conditions.

Baseline expression of the TM gene expression by endothelial cells in static culture will be determined by quantitative real-time PCR using an ABI Prism 7700 Sequence Detector employing rabbit TM-specific probes and primers. Endothelial cells will be seeded onto 2 mm Dacron graft segments (Meadox Medicals, Oakland, N.J.) using previously described methods (V. Shayani et al. (1994) *J Surg Res* 57:495) and perfused under low and high shear stress for periods ranging between 1 and 7 days. Endothelial cells will be removed from the graft by collagen digestion and the RNA extracted, and cDNA will be generated using reverse transcriptase. The level of TM expression will be normalized to ribosomal RNA.

We anticipate that endothelial cell TM gene expression will be decreased after expansion in static culture followed by exposure to arterial shear stress. To augment TM expression, endothelial cells will be transduced ex vivo with either no virus, G1ShTM, a retrovirus vector expressing human TM, or G1SAMEN, an identical retrovirus vector expressing no transgene (generously supplied by Dr. R. Morgan, NCHGR, NIH). After appropriate selection in G-418 (Life Technologies), the amount of both human and rabbit TM gene expression will be quantified using real-time pCR employing species-specific TM primers and probes. Cells will then be seeded onto vascular grafts and perfused under low and high shear stress for periods ranging between 1 and 7 days. Endothelial cells will be harvested and any change in total TM (rabbit+human) gene expression will be compared between the treatment groups.

It is anticipated that retroviral-mediated transfer of the TM gene is an efficacious method by which preservation and augmentation of TM expression and activity can be achieved in endothelial cells used for seeding prosthetic vascular grafts. These results will permit initiation of experiments to determine whether seeding of prosthetic grafts with genetically-modified endothelial cells can improve graft patency in vivo.

Evidence from a rabbit model of human vein graft disease (Example-1) demonstrates that TM expression by the venous endothelium is dramatically reduced following implantation into the arterial circulation (Example-2). Loss of TM expression results in a reduced capacity of the graft to generate APC with consequent enhancement of local thrombin activation. This novel finding may explain the high rate at which human vein grafts develop occlusive thrombosis in the first few months after implantation.

The concept that viral-mediated transfer of TM to vein grafts might prevent vein graft failure (Example-4 and -5) does not inherently follow from this prior work for the following reasons: 1) Long-term reductions in the in vivo expression of native TM have not previously been demonstrated, nor expected, following implantation of vein grafts into the arterial circulation. 2) Reduced TM expression has not been demonstrated to be temporally associated with enhanced local thrombin generation in vein grafts. 3) Enhanced thrombin activation, as a cause of early vein graft thrombosis, has not been previously demonstrated. 4) Restoration of TM expression has not previously been demonstrated to prevent local thrombin activation. 5) Enhanced TM expression has not been previuosly demonstrated to prevent the development of accelerated atherosclerosis in vein grafts.

All references disclosed herein including the following specific references are incorporated by reference. The following references are specifically incorporated by reference:
1. Virmani R. et al. (1988) *Cardiovasc. Clinics* 18:41.
2. Rutherford J. Braunwald E: (1992) Chronic Ischemic Heart Disease
3. Lytle B W, et al. (1985) *J Thorac Cardiovasc Surg* 89:248-258
4. Cameron A, et al. (1996) *N Engl J Med* 334:216-219
5. Angelini G D, Newby A C (1989) *Eur Heart J* 10:273-280
6. Cox J L, et al. (1991) *Prog Cardiovasc Dis* 34:45-68
7. Osterud B (1999) *Thromb Haemost* 78:755-758
8. Maruyama I (1992) *Jpn Circ J* 56:187-191
9. Wilcox J N (1991) *Circulation* 84:432-435
10. Nikkari S T, Clowes A W (1994) *Ann Med* 26:95-100
11. Schwarb: S M, et al. (1995) *Circ Res* 77:445465
12. Fuster V (1986) *J Cardiol* 73:292-305
13. Fager G (1995) *Circ Res* 77:645-650
14. Kalan J M, Roberts W C (1990) *Am Heart J* 119: 1164-1184
15. Walts A K, et al. (1987) *Am Heart J* 114:718-723
16. Mann M, et al. (1995) *Proc Natl Acad Sci USA* 92:4502-506
17. Markwardt F (1970) *Methods Enzymol* 19:924-932
18. Weitz J I, et al. (1990) *J Clin Invest* 86:385-391
19. Bar-Shavit R. et al. (1989) *J Clin Invest* 84:1096-1104
20. Just M, et al. (1991) *Haemostasis* 21 (suppl 1):80-87
21. Sarembock I J, et al. (1991) *Circulation* 84:232-243
22. Gallo R., et al.(1998) *Circulation* 97:581-588.
23. Gerdes C, et al. (1996) *Arterioscler Thromb Vasc Biol* 16:1306-1311
24. Abendschein D R, et al. (1996) *J Am Coll Cardiol* 28:1849-1855
25. Ragosta M, et al. (1996) *Circulation* 93: 1194-1200
26. Serruys P., et al. (1995) *N Engl J Med* 333:757-763
27. Bittl J A, et al. (1995) *N Engl J Med* 333:764-769
28. Dittman W A, Majerus P W: (1990) *Blood* 75:329-336
29. Zhang Y., et al. (1998) *J Clin Invest* 10:1301-1309
30. Grinnell B W, Berg D T: (1999) *Am J Physiol* 270:H603-H609
31. Lafay M, et al. (1998) *Thromb Haemost* 79:848-852
32. Cadroy Y., et al. (1997) *Arterioscler Thromb Vasc Biol* 17:520-527
33. Moore K L, et al. (1989) *Blood* 73: 159-165
34. Nawroth P P, et al. (1986) *Proc Natl Acad Sci USA* 83:3460-3464
35. Ohji T., et al. (1995) *Thromb Haemost* 73:812-818
36. Nishida K, et al. (1998) *J Surg Res* 79:85-90
37. Broze G: (1998) *Thrombosis and Hemorrhage.* pp 77-104
38. Nwasokwa O N (1995) *Ann Int Med* 123:528-545
39. Channon K M, et al. (1997) *Arterioscler Thromb Vasc Biol* 17:1313-1319
40. Cook J M, et al. (1991) *J Vasc Surg* 14:147-151
41. Gosling M, et al.(1999) *Circulation* 99:1047-1053
42. Nabel K G, et al. (1994) *Cardiovasc Res* 28:445-455

43. Rade J J, et al. (1996) *Nat Med* 2:293-298
44. Hatton M W C, et al. (1994) *Thromb Haemost* 71:499-506
45. Jackman R W, et al. (1998) *Hum Gene Ther* 9:1069-1081
46. Kupfer J M, et al. (1996) *Circulation* 94 (suppl 1):741
47. Waugh J M, et al. (1999) *Circ Res* 84:84-92
48. Kohler T., et al.(1990) *Am J Surg* 160:257-260
49. Dobrin P B, et al. (1989) *Surgery* 105:393400
50. Zwolak R M, et al. (1987) *J Vasc Surg* 5:126-
51. Zwolak R M, et al.(1989) *Artenoscler* 9:37
52. Golledge J., et al.(1997) *J Clin Invest* 99:2719
53. Soyombo A A, et al. (1990) *Am J Pathol* 137:1401
54. Soyombo A A, et al. (1993) *Cardiovasc Res* 27:1961
55. Soyombo A A, et al. (1995) *J Thorac Cardiovasc Surg* 109:2
56. Baker A H, et al. (1997) *Cardiovasc Res* 35:442
57. George S J, et al. (1996) *Arterioscler* 120:227
58. George S J, et al. (1998) *Hum Gene Ther* 9:867
59. George S J, et al. (1998) *Gene Therapy* 5:1552
60. Hardy S., et al. (1997) *J Virol* 71: 1842-1849
61. Lee S W, et al. (1993) *Circ Res* 73:197-807
62. Nabel K G, et al. (1993) *Proc Natl Acad Sci USA* 90:10759-10763.
63. Kotin R M: (1994) *Hum Gene Ther* 5:793-801
64. Kaplitt M G, et al. (1994) *Nature Genencs* 8:148-154
65. Podsakoff G., et al. (1994) *J Virol* 68:5656-5666.
66. Bantel-Schaal A, Stohr M (1992) *J Virol* 66:773-778
67. Gnatenko D, et al. (1997) *J Clin Invest* 45:87-98
68. Rolling F., et al. (1997) *Gene Therapy* 4:757-761
69. Chiorim J C, et al. (1995) *Hum Gene Ther* 6:1531-1541
70. Flotte 1X, et al. (1992) *Am J Respir Cell Mol. Biol* 7:349-356
71. Summerford C, Sarnulski R J (1998) *J Virol* 72:1438-1445 m
72. Rome J J, et al. (1994) *Hum Gene Ther* 5:1249-1258
73. Schulick A H, et al. (1995) *Circ Res* 77:475-485~I
74. Lynch C, et al. (1997) *Circ Res* 80:497-505 1~I
75. Ferrari F K, et al. (1996) *J Virol* 70:3227-3234
76. Fisher K J, et al. (1996) *J Virol* 70:520-532
77. Esmon C T (2000) *Thromb Haemost* 2000;83 :639-643
78. Xu J., et al. (1999) *J Biol Chem* 274:6704-6710
79. Waugh J M, et al. (2000) *Circulation* 102:332-337
80. Davies M G, et al. (1993) *Eur J Vasc Surg* 7: 156-165
81. Champion H C, et al. (1999) *Circ Res* 84:1422-1432
82. Fukudome K, Esmon C T (1994) *J Biol Chem* 269: 26486-26491
83. Fukadome K, Esmon C T (1995) *J Biol Chem* 270:5571-5577
84. Wang J., et al. (1999) *DNA Res* 26:57-62
85. Kurosawa S., et al. (1988) *J Biol Chem* 263:5993-5996
86. Newman K D, et al. (1995) *J Clin Invest* 96:2955-2965
87. Wen S., et al.(2000) *Arterioscler Thromb Vasc Biol* 20: 1452-1458
88. Fukudome K, et al. (1996) *J Biol Chem* 271:17491-17498
89. Morgan R A, et al. (1992) *Nucleic Acid Res* 20:1293-1299
90. AnonymousComparison (1997) *J Gen Virol* 78: 1653-1661
91. Bartlett J S, et al. (1996) *Proc Natl Acad Sci USA* 93:8852-8857
92. Cowan P J, et al. (1991) *J Biol Chem* 273:11737-11744
93. Willerson J T, et al. (1991) *Proc Natl Acad. Sci USA* 88 10624-10628

While the invention has been described with reference to specific embodiments, modifications and variations of the invention may be constructed without departing from the scope of the invention, which is defined in the following claims.

What is claimed is:

1. A method for treating a mammal to resist early vein graft failure comprising,
    a) introducing into endothelial cells of an autologous vein graft from the mammal an effective amount of at least one nucleic acid encoding one of the following agents: thrombomodulin (TM), NF-κB inhibitor, or a functional fragment of the TM; provided that when the agent is thrombomodulin, the nucleic acid further encodes the NF-κB inhibitor, wherein the introducing is performed ex vivo or by direct injection into the graft, and
    b) transplanting the vein graft into the mammal when the introducino is performed ex vivo.

2. A method for engineering a vein graft of a mammal to resist early graft failure, the method comprising:
    a) introducing into endothelial cells of an autologous vein graft from the mammal an effective amount of at least one nucleic acid encoding one of the following agents: thrombomodulin (TM), NF-κB inhibitor, or a functional fragment of the TM; provided that when the agent is thrombomodulin, the nucleic acid further encodes the NE-κB inhibitor, wherein the introducing is performed ex vivo or by direct injection into the graft, and,
    b) transplanting the vein graft into the mammal when the introducing is performed ex vivo.

3. The method of claim 1 or 2, wherein the introducing is performed on the graft in vivo.

4. The method of claim 1 or 2, wherein the transplanted graft has sufficient activated protein C (APC) activation as determined by a standard protein C assay to prevent or treat the early graft failure.

5. The method of claim 4, wherein the level of protein C activation as determined by a standard protein C detection assay of the treated graft is at least about one order of magnitude higher than a control vessel.

6. The method of claim 5, wherein the higher protein C level of the treated vascular graft is detectable for at least about a week.

7. The method of claim 4, wherein the early graft failure is accompanied by thrombosis.

8. The method of claim 1 or 2, wherein the nucleic acid is inserted into a cassette.

9. The method of claim 8, wherein the cassette includes a promoter.

10. The method of claim 9, wherein the cassette is inserted into a vector.

11. The method of claim 10, wherein the vector comprises sequence from an adenovirus, retrovirus, or adeno-associated virus.

12. The method of claim 11, wherein the vector is a replication defective adenovirus.

13. The method of claim 1, wherein the nucleic acid encodes at least one other anticoagulant molecule.

14. The method of claim 13, wherein the anticoagulant molecule is thrombomodulin or a functional fragment thereof.

15. The method of claim 1 or 2, wherein the mammal is susceptible to an inflammatory or immunological stimulus and the method further comprises administering a therapeutic amount of at least one anti-coagulant, antithrombotic, or thrombolytic drug to treat or prevent that stimulus.

16. The method of claim 15, wherein the drug is administered before step a) or after step b) of the method.

17. The method of claim 16, wherein the anti-coagulant drug is coumadin.

18. An engineered vein graft produced by the method of claim 2.

19. The engineered vein graft of claim 18, wherein the vessel is an autologous saphenous vein graft (SVG).

20. A method for treating a mammal to resist early vein graft failure comprising,
   a) introducing into endothelial cells of an autologous vein graft from the mammal an effective amount of at least one nucleic acid encoding at least one of the following agents: thrombomodulin (TM), NF-κB inhibitor, or a functional fragment of the TM; provided that when the agent is thrombomodulin, the nucleic acid further encodes the NF-κB inhibitor, wherein the introducing is performed ex vivo or by direct injection into the graft, the nucleic acid being expressed from a recombinant adenovirus vector comprising a first adenovirus inverted terminal repeat (ITR) operably linked to the nucleic acid, and
   b) transplanting the vein graft into the mammal when the introducing is performed ex vivo.

21. The method of claim 20, wherein the recombinant adenovirus vector further comprises a cytomeglovirus promoter operably linked to the nucleic acid.

22. The method of claim 20 or 21, wherein the recombinant adenovirus vector further comprises a second ITR operably linked to the nucleic acid.

23. The method of claim 20, wherein the recombinant adenovirus vector is AdTMh5.

24. A method for treating a mammal to resist early vein graft failure comprising,
   a) introducing into endothelial cells of an autologous vein graft from the mammal an effective amount of at least one nucleic acid encoding at least one of the following agents: thrombomodulin (TM), NF-κB inhibitor, or a functional fragment of the TM; provided that when the agent is thrombomodulin, the nucleic acid further encodes the NF-κB inhibitor, wherein the introducing is performed ex vivo or by direct injection into the graft, the nucleic acid being expressed from a recombinant adeno-associated virus (AAV) vector and operably linked to an adeno-associated virus inverted terminal repeat (ITR), and
   b) transplanting the vein graft into the mammal when the introducing is performed ex vivo.

25. The method of claim 24, wherein the AAV vector further comprises an operably linked Rous sarcoma virus long terminal repeat promoter.

26. The method of claim 25, wherein the AAV vector is $AAV_2hTM$.

27. The method of any one of claims 1, 2, 20, or 24 further comprising introducing into cells of the graft a nucleic acid encoding thrombomodulin (TM) or a functional fragment thereof.

28. The engineered graft of claim 18 further comprising cells comprising an introduced nucleic acid encoding thrombomodulin (TM) or a functional fragment thereof.

* * * * *